United States Patent [19]

Komyoji et al.

[11] Patent Number: 5,436,267
[45] Date of Patent: Jul. 25, 1995

[54] N-PHENYLCARBAMATE COMPOUND, PROCESS FOR PREPARING THE SASME AND BIOCIDAL COMPOSITION FOR CONTROL OF HARMFUL ORGANISMS

[75] Inventors: Terumasa Komyoji; Itaru Shigehara; Norifusa Matsuo; Hiroshi Shimoharada; Takeshi Ohshima; Toshio Akagi; Shigeru Mitani, all of Shiga, Japan

[73] Assignee: Ishihara Sangyo Kaisha, Ltd., Osaka, Japan

[21] Appl. No.: 272,624

[22] Filed: Jul. 11, 1994

Related U.S. Application Data

[63] Continuation of Ser. No. 831,877, Feb. 6, 1992, abandoned.

[30] Foreign Application Priority Data

Feb. 7, 1991 [JP] Japan ................... 3-102220
Oct. 23, 1991 [JP] Japan ................... 3-304176

[51] Int. Cl.⁶ ............... A01N 43/56; C07D 231/70; C07F 7/10
[52] U.S. Cl. ................... 514/485; 514/488; 514/520; 514/522; 514/525; 514/331; 514/367; 514/375; 514/399; 514/400; 514/258; 548/217; 548/309.7; 548/180; 546/195; 544/279; 560/27
[58] Field of Search ............... 514/485, 488, 520, 522, 514/525, 331, 367, 375, 399, 400, 258; 548/217, 309.7, 180; 546/194; 544/279; 560/27; 558/392

[56] References Cited

U.S. PATENT DOCUMENTS

| | | | |
|---|---|---|---|
| 4,831,041 | 5/1989 | Shiokawa et al. | 514/300 |
| 4,843,068 | 6/1989 | Hamaguchi et al. | 514/63 |
| 4,996,217 | 2/1991 | Honma | 514/338 |

FOREIGN PATENT DOCUMENTS

| | | | |
|---|---|---|---|
| 0091639 | 10/1983 | European Pat. Off. | 560/24 |
| 268989 | 6/1988 | European Pat. Off. | |
| 0270091 | 6/1988 | European Pat. Off. | 560/24 |
| 0397345 | 11/1990 | European Pat. Off. | 560/24 |
| 2412520 | 12/1978 | France | 560/24 |
| 3020784 | 12/1981 | Germany | 560/24 |
| 50-151889 | 12/1975 | Japan . | |

OTHER PUBLICATIONS

*Tetrahedron Letters*, vol. 29, No. 15, pp. 1799–1802, (1988).
*Chem. Pharm. Bull.*, 36 (4), pp. 1305–1308 (1988).
*Journal of Medicinal Chemistry*, 1970, vol. 13, No. 4, pp. 713–722.
*Ingenineria Y Ciencia Quimica*, 1979. 3(3), pp. 132–133.
*Journal fur Praktisch Chemie.*, 4. Reihe., Band 12. pp. 44–49, 1960.

Primary Examiner—Marianne M. Cintins
Assistant Examiner—Keith MacMillan
Attorney, Agent, or Firm—Sughrue, Mion, Zinn, Macpeak & Seas

[57] ABSTRACT

A novel N-phenylcarbamate compound or its salt where possible, which is useful as the active ingredient of a biocidal composition for control of harmful organisms, is represented by the following general formula (I):

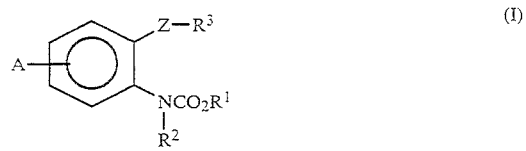

wherein $R^1$ is unsubstituted or substituted alkyl; $R^2$ is H, unsubstituted or substituted alkyl, alkenyl, alkynyl or cycloalkyl, or $—COX^1$ wherein $X^1$ is unsubstituted or substituted alkyl, alkenyl, alkynyl, cycloalkyl or alkoxy; Z is $—CH_2S—$, $—SCH_2—$, $—CH_2O—$, $—OCH_2—$, $—CH_2CH_2—$, $—CH=CH—$, $—C\equiv C—$, $—CH_2SO—$, $—CH_2SO_2—$, $—CH_2SCH_2—$, or $—CH_2O—N=C(R^4)—$; $R^3$ is unsubstituted or substituted phenyl, pyridyl, benzothiazolyl, benzoxazolyl, benzimidazolyl, imidazopyridyl, naphthyl, pyrimidinyl, thienyl, furyl, thiazolinyl, oxazolinyl, pyrazinyl, thiazolyl, oxazolyl, imidazolyl, pyrazolyl, quinolyl, indolyl, pyrrolyl, benzofuryl, benzothienyl, indanyl, tetrahydronaphthyl, dihydrobenzofuryl, dihydrobenzothienyl, benzoxazinyl, benzothiazinyl or benzoyl.

7 Claims, No Drawings

N-PHENYLCARBAMATE COMPOUND, PROCESS FOR PREPARING THE SASME AND BIOCIDAL COMPOSITION FOR CONTROL OF HARMFUL ORGANISMS

This is a Continuation of application Ser. No. 07/831,877 filed Feb. 6, 1992, now abandoned.

FIELD OF THE INVENTION

The present invention relates to an N-phenylcarbamate compound or its salt where possible, processes for preparing the same, and an agricultural biocidal composition (pesticide) comprising the same for controlling harmful organisms (pest control).

BACKGROUND OF THE INVENTION

N-phenylcarbamate compounds are described in, for example, (1) Japanese Patent Laid-Open No. 146,881/1988 which corresponds to EP-A-268,989 and U.S. Pat. No. 4,831,041; (2) Japanese Patent Laid-Open No. 131,175/1989 which corresponds to EP-A-270,091 and U.S. Pat. No. 4,996,217; (3) *Tetrahedron Letters*, Vol. 29, No. 15, pp. 1799–1802, 1988; (4) *Journal fur Praktische Chemie.*, 4. Reihe., Band 12. pp. 44–49, 1960; (5) *Chem. Pharm. Bull.*, 36 (4), pp. 1305–1308 (1988); (6) *INGENIERIA Y CIENCIA QUIMICA*, 1979, 3 (3), pp. 132–133; (7) Japanese Patent Laid-Open No. 151,889/1975; (8) *Journal of Medicinal Chemistry*, 1970, Vol. 13, No. 4, pp. 713–722; etc. However, all of them fail to disclose such N-phenylcarbamate compounds as represented by the general formula (I) mentioned below according to the present invention.

SUMMARY OF THE INVENTION

In accordance with one aspect of the present invention, there is provided an N-phenylcarbamate compound represented by the following general formula (I) or its salt where possible:

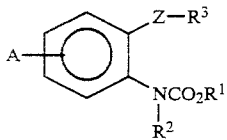

(I)

wherein $R^1$ is an unsubstituted or substituted alkyl group; $R^2$ is a hydrogen atom, an unsubstituted or substituted alkyl group, an unsubstituted or substituted alkenyl group, an unsubstituted or substituted alkynyl group, an unsubstituted or substituted cycloalkyl group, or a —$COX^1$ group wherein $X^1$ is an unsubstituted or substituted alkyl group, an unsubstituted or substituted alkenyl group, an unsubstituted or substituted alkynyl group, an unsubstituted or substituted cycloalkyl group, or an unsubstituted or substituted alkoxy group; Z is a —$CH_2S$— group, an —$SCH_2$— group, a —$CH_2O$— group, an —$OCH_2$— group, a group, a —$CH_2CH_2$— group, a —CH=CH— group, a —C≡C— group, a —$CH_2SO$— group, a —$CH_2SO_2$— group, a —$CH_2SCH_2$— group, or a —$CH_2O$—N=$C(R^4)$— group, the right hyphen of each of which represents a bond directed toward $R^3$; $R^3$ is an unsubstituted or substituted phenyl group, an unsubstituted or substituted pyridyl group, an unsubstituted or substituted benzothiazolyl group, an unsubstituted or substituted benzoxazolyl group, an unsubstituted or substituted benzimidazolyl group, an unsubstituted or substituted imidazopyridyl group, an unsubstituted or substituted naphthyl group, an unsubstituted or substituted pyrimidinyl group, an unsubstituted or substituted thienyl group, an unsubstituted or substituted furyl group, an unsubstituted or substituted thiazolinyl group, an unsubstituted or substituted oxazolinyl group, an unsubstituted or substituted pyrazinyl group, an unsubstituted or substituted thiazolyl group, an unsubstituted or substituted oxazolyl group, an unsubstituted or substituted imidazolyl group, an unsubstituted or substituted pyrazolyl group, an unsubstituted or substituted quinolyl group, an unsubstituted or substituted indolyl group, an unsubstituted or substituted pyrrolyl group, an unsubstituted or substituted benzofuryl group, an unsubstituted or substituted benzothienyl group, an unsubstituted or substituted indanyl group, an unsubstituted or substituted tetrahydronaphthyl group, an unsubstituted or substituted dihydrobenzofuryl group, an unsubstituted or substituted dihydrobenzothienyl group, an unsubstituted or substituted benzoxazinyl group, an unsubstituted or substituted benzothiazinyl group, or an unsubstituted or substituted benzoyl group; $R^4$ is a hydrogen atom, an unsubstituted or substituted alkyl group, an unsubstituted or substituted cycloalkyl group, an unsubstituted or substituted alkoxy group, an unsubstituted or substituted alkylthio group, an unsubstituted or substituted phenyl group, a cyano group, an —$NR^5R^6$ group, or a —$CO_2R^7$ group; $R^5$ and $R^6$ are either each independently a hydrogen atom or an unsubstituted or substituted alkyl group, or combined with each other to form a 5- to 7-membered heterocyclic group together with the adjacent nitrogen atom; $R^7$ is an unsubstituted or substituted alkyl group; and A is a hydrogen atom, a halogen atom, an unsubstituted or substituted alkyl group, an unsubstituted or substituted alkoxy group, an unsubstituted or substituted phenoxy group, or an unsubstituted or substituted pyridyloxy group; provided (1) that $R^2$ is a hydrogen atom when Z is a —$CH_2SO$— group or a —$CH_2SO_2$— group, and (2) that an exception is made of the case (i) where $R^1$ is a methyl group, $R^2$ is a hydrogen atom and —Z—$R^3$ group is a 2-nitro-3-pyridyloxymethyl group, a phenylethynyl group, a styryl group or a 2-bromobenzyloxy group, and the case (ii) where $R^1$ is an ethyl group, $R^2$ is a hydrogen atom and —Z—$R^3$ is a benzyloxy group, a phenylethynyl group, a styryl group or a 2-bromobenzylthio group.

In accordance with another aspect of the present invention, there are provided processes for preparing an N-phenylcarbamate compound as represented by the above-mentioned general formula (I) or its salt where possible, which are detailed hereinafter.

In accordance with still another aspect of the present invention, there is provided a biocidal composition comprising as the effective ingredient an N-phenylcarbamate compound as represented by the general formula (I) or its salt where possible, which is detailed hereinafter.

Substituents of the substituted alkyl, alkenyl, alkynyl, cycloalkyl, alkoxy, or alkylthio group included in the denotation of at least one of $R^1$, $R^2$, $X^1$, $R^4$, $R^5$, $R^6$, $R^7$, or A in the general formula (I) include halogen atom; cyano group; alkoxy group unsubstituted or substituted with at least one halogen atom and/or at least one alkoxy group; alkylthio group; alkoxycarbonyl group; alkylcarbonyl group; or cycloalkyl group; nitro group; and phenyl group. Where the number of such substituents is 2 or more, the substituents may be either the same or different from each other.

Substituents of the substituted phenyl, pyridyl, benzothiazolyl, benzoxazolyl, benzimidazolyl, imidazopyridyl, phenoxy, pyridyloxy, naphthyl, pyrimidinyl, thienyl, furyl, thiazolinyl, oxazolinyl, pyrazinyl, thiazolyl, oxazolyl, imidazolyl, pyrazolyl, quinolyl, indolyl, pyrrolyl, benzofuryl, benzothienyl, indanyl, tetrahydronaphthyl, dihydrobenzofuryl, dihydrobenzothienyl, benzoxazinyl, benzothiazinyl, or benzoyl group included in the denotation of at least one of $R^3$, $R^4$, and A include, for example, halogen atom; alkyl group unsubstituted or substituted with at least one halogen atom and/or at least one alkoxy group and/or at least one alkoxyimino group; nitro group; cyano group; alkoxycarbonyl group; alkoxy group unsubstituted or substituted with at least one halogen atom; alkylenedioxy group unsubstituted or substituted with at least one halogen atom and/or at least one alkoxy group and/or at least one alkyl group; alkylsulfonyloxy group unsubstituted or substituted with at least one halogen atom; alkylthio group; alkylsulfonyl group; alkylsulfinyl group; aryl group such as phenyl group and naphthyl group; pyrrolyl group unsubstituted or substituted with at least one alkyl group; (2-tetrahydropyranyl)oxy group; carbamoyl group unsubstituted or substituted with at least one alkyl group; pyridyloxy group unsubstituted or substituted with at least one halogen atom and/or at least one trifluoromethyl group; dialkylamino group; and alkylcarbonyloxy group. Where the number of such substituents is 2 or more, the substituents may be either the same or different from each other.

As the alkyl group or alkyl moiety that is as well as may be included in the general formula (I), there can be mentioned, for example, those having 1 to 6 carbon atoms, such as methyl group, ethyl group, propyl group, butyl group, pentyl group, and hexyl group. As the alkenyl group or alkenyl moiety that may be included in the general formula (I), there can be mentioned, for example, those having 2 to 6 carbon atoms, such as vinyl group, propenyl group, butenyl group, pentenyl group, and hexenyl group. As the alkynyl group or alkynyl moiety that may be included in the general formula (I), there can be mentioned, for example, those having 2 to 6 carbon atoms, such as ethynyl group, propynyl group, butynyl group, pentynyl group, and hexynyl group. These groups or moieties mentioned above encompass structurally isomeric ones having a linear or branched aliphatic chain. As the cycloalkyl group or cycloalkyl moiety that may be included in the general formula (I), for example, in the denotation of $R^2$, there can be mentioned, for example, those having 3 to 6 carbon atoms, such as cyclopropyl group, cyclobutyl group, cyclopentyl group, and cyclohexyl group.

As the halogen atom that may included in the general formula (I), there can be mentioned, for example, fluorine atom, chlorine atom, bromine atom, and iodine atom.

$R^5$ and $R^6$ may be combined with each other to form a 5- to 7-membered heterocyclic group together with the adjacent nitrogen atom. Examples of such a 5- to 7-membered heterocyclic group include saturated heterocyclic groups such as morphorino group, pyrrolidino group, and piperidino group; and unsaturated heterocyclic groups such as triazolyl group and imidazolyl group.

Where $R^3$ is an unsubstituted or substituted pyridyl group, an unsubstituted or substituted benzothiazolyl group, an unsubstituted or substituted benzoxazolyl group, an unsubstituted or substituted benzimidazolyl group, an unsubstituted or substituted imidazopyridyl group, an unsubstituted or substituted pyrimidinyl group, an unsubstituted or substituted pyrazinyl group, an unsubstituted or substituted thiazolyl group, an unsubstituted or substituted oxazolyl group, an unsubstituted or substituted imidazolyl group, or an unsubstituted or substituted quinolyl group, the compound of the formula (I) may be turned into the form of a salt with an acidic substance. Examples of such a salt include inorganic acid salts such as hydrochloride and sulfate.

Where Z is a —CH=CH— group or a —CH$_2$O—N=C($R^4$)— group, the compound of the formula (I) involves geometrical isomers in an E form and in a Z form because of the double bond contained therein. In this case, the compound of the present invention encompasses an E isomer, a Z isomer, and a mixture thereof.

Among those compounds as represented by the general formula (I) according to the present invention, the following compounds are preferred.

(1) Compounds of the formula (I) wherein Z is a —CH=CH— group or a —CH$_2$O—N=C($R^4$)— group and $R^4$ is a hydrogen atom, an unsubstituted or substituted alkyl group, an unsubstituted or substituted alkoxy group, an unsubstituted or substituted alkylthio group, or their salts where possible;

(2) Compounds of the formula (I) wherein $R^2$ is a hydrogen atom, an unsubstituted or substituted alkyl group, an unsubstituted or substituted alkynyl group or a —COX$^1$ group, and X$^1$ is an unsubstituted or substituted alkyl group, or their salts where possible; and (3) Compounds of the formula (I) wherein $R^3$ is an unsubstituted or substituted phenyl group, an unsubstituted or substituted pyridyl group, an unsubstituted or substituted thienyl group, an unsubstituted or substituted furyl group, an unsubstituted or substituted indanyl group, or an unsubstituted or substituted dihydrobenzofuryl group, or their salts where possible.

More preferred are compounds of the formula (I) wherein $R^2$ is an unsubstituted or substituted alkyl group, Z is a —CH$_2$O—N=C($R^4$)— group, $R^3$ is an unsubstituted or substituted phenyl group, an unsubstituted or substituted pyridyl group, an unsubstituted or substituted thienyl group, an unsubstituted or substituted furyl group, an unsubstituted or substituted indanyl group, or an unsubstituted or substituted dihydrobenzofuryl group, and $R^4$ is an unsubstituted or substituted alkyl group; and compounds of the formula (I) wherein $R^2$ is a hydrogen atom or an unsubstituted or substituted alkyl group, Z is a —CH=CH— group, and $R^3$ is an unsubstituted or substituted phenyl group. A methyl group, an ethyl group and a methoxymethyl group are more preferred as the unsubstituted or substituted alkyl group which $R^2$ may stand for. A methyl group is more preferred as the unsubstituted or substituted alkyl group which $R^4$ may stand for.

The compound of the general formula (I) can be prepared, for example, according to one of the following Reaction Processes 1 to 6.

(i) Where Z is Z' which stands for a —CH$_2$S— group, an —SCH$_2$— group, a —CH$_2$O— group, an —OCH$_2$— group, a —CH$_2$CH$_2$— group, a —CH=CH— group, a —C≡C— group, a —CH$_2$SCH$_2$— group or a —CH- $_2O$—N=C($R^4$)— group, and $R^4$ is as defined above, the compound of the formula (I) can be prepared, for example, according to one of the following Reaction Processes 1 to 3;

Reaction Process 1

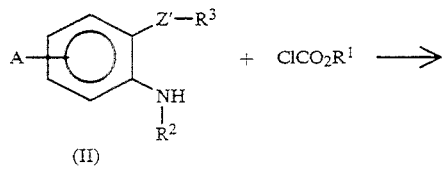

(II)

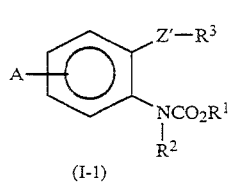

(I-1)

Reaction Process 2

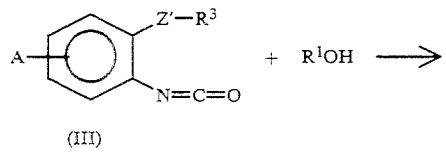

(III)

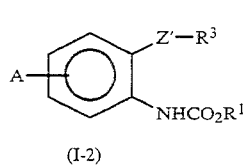

(I-2)

Reaction Process 3

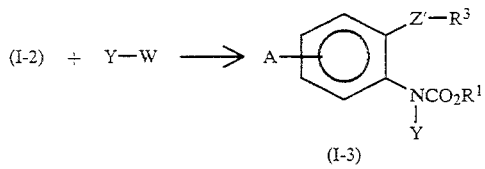

(I-3)

In the formulae of the above-mentioned Reaction Processes 1 to 3, $R^1$, $R^2$, $Z'$, $R^3$ and A are the same as defined above; Y is an unsubstituted or substituted alkyl group, an unsubstituted or substituted alkenyl group, an unsubstituted or substituted alkynyl group, an unsubstituted or substituted cycloalkyl group, or a —$COX^1$ group wherein $X^1$ is an unsubstituted or substituted alkyl group, an unsubstituted or substituted alkenyl group, an unsubstituted or substituted alkynyl group, an unsubstituted or substituted cycloalkyl group, or an unsubstituted or substituted alkoxy group; and W is a chlorine atom, a bromine atom or an iodine atom.

In the Reaction Process 3, $(X^2CO)_2O$ wherein $X^2$ is an unsubstituted or substituted alkyl group, an unsubstituted or substituted alkenyl group, an unsubstituted or substituted alkynyl group, or an unsubstituted or substituted cycloalkyl group may be used in place of Y—W when Y is —$COX^2$ wherein $X^2$ is the same as defined above.

(ii) Where Z is a —$CH_2SO$— group or a —$CH_2SO_2$— group, the compound of the formula (I) can be prepared, for example, according to the following Reaction Process 4:

Reaction Process 4

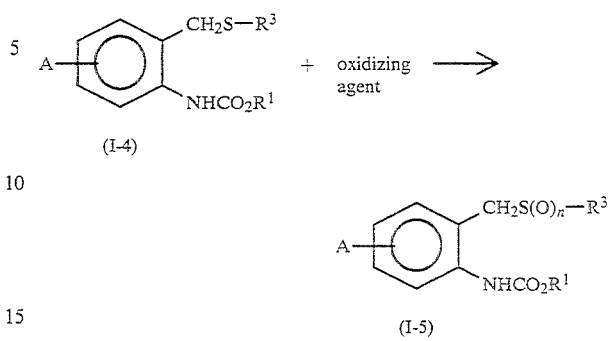

In the formula of the Reaction Process 4, $R^1$, $R^3$ and A are the same as defined above and n is an integer of 1 or 2.

(iii) Where $R^2$ is a hydrogen atom and Z is a —$CH_2O$— group, a —$CH_2S$— group, a —$CH_2SCH_2$— group or a —$CH_2O$—N=C($R^4$)— group, the compound of the formula (I) can be prepared, for example, according to the following Reaction Process 5:

Reaction Process 5

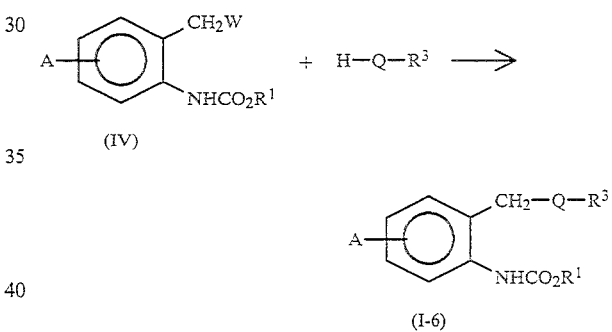

In the formula of the Reaction Process 5, $R^1$, $R^3$, A and W are the same as defined above, Q is an oxygen atom, a sulfur atom, an —$SCH_2$— group, or an —O—N=C($R^4$)— group, and the hyphen on the right side of Q represents a bond directed toward $R^3$, provided that an exception is made of the case where $R^1$ is a methyl group and a —Q—$R^3$ group is a 2-nitro-3-pyridyloxy group.

(iv) Where $R^2$ is a hydrogen atom and Z is a —C≡C— group, the compound of the formula (I) can be prepared, for example, according to the following Reaction Process 6 similar to the method as described, for example, in Chem. Pharm. Bull., 36 (4), pp. 1305–1308 (1988).

Reaction Process 6

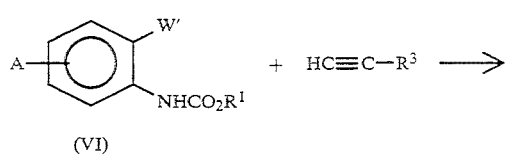

(VI)

-continued
Reaction Process 6

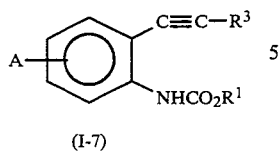

(I-7)

In the formula of the Reaction Process 6, $R^1$, $R^3$ and A are as defined above, and W' is a bromine atom or an iodine atom.

The compound represented by the general formula (II) that is used in the Reaction Process 1 can be prepared, for example, according to the following Reaction processes 7 to 12 in the case where $R^2$ in the formula (II) is a hydrogen atom.

(i) Where Z is a —$CH_2O$— group, a —$CH_2S$— group, a —$CH_2SCH_2$— group or a —$CH_2O$—$N$=$C(R^4)$— group, the compound of the formula (II) can be prepared, for example, according to the following Reaction Process 7:

Reaction Process 7

(1)

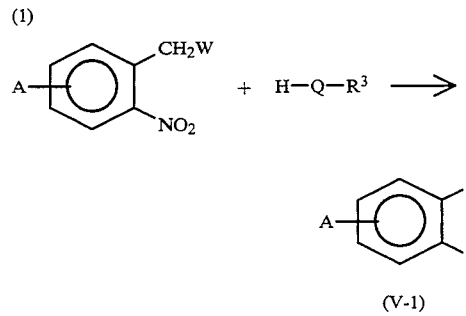

(V-1)

(2)

(V-1) $\xrightarrow{\text{reduction}}$ (II-1)

In the formula of the Reaction Process 7, A, W, Q and $R^3$ are the same as defined above.

(ii) Where Z is an —$OCH_2$— group or an —$SCH_2$— group, the compound of the formula (II) can be prepared, for example, according to the following Reaction Process 8:

Reaction Process 8

(1)

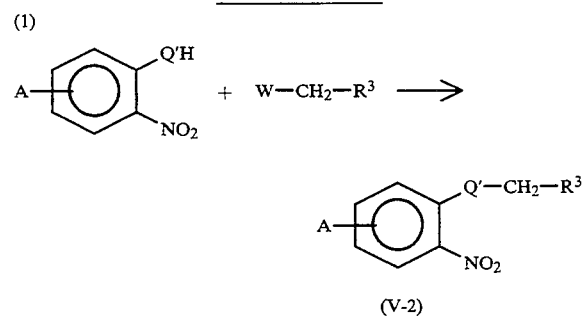

(V-2)

(2)

-continued
Reaction Process 8

(V-2) $\xrightarrow{\text{reduction}}$ (II-2)

In the formula of the Reaction Process 8, A, W and $R^3$ are the same as defined above, and Q' is an oxygen atom or a sulfur atom.

(iii) Where Z is a —CH=CH— group, the compound of the formula (II) can be prepared, for example, according to the Reaction Process 9:

Reaction Process 9

(1)

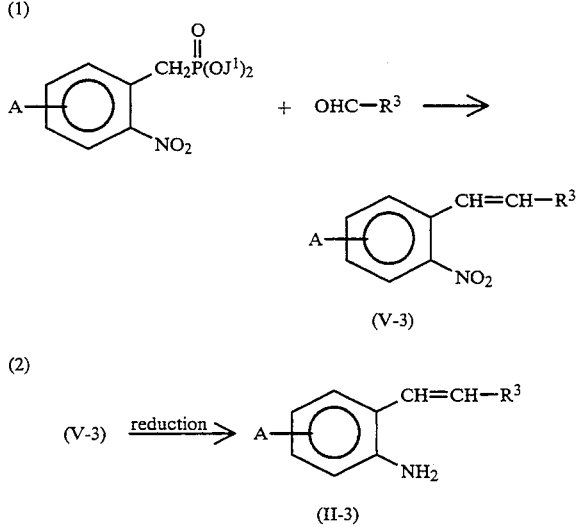

(V-3)

(2)

(V-3) $\xrightarrow{\text{reduction}}$ (II-3)

In the formula of the Reaction Process 9, $R^3$ and A are the same as defined above, and $J^1$ is a methyl group or an ethyl group.

(iv) Where Z is a —$CH_2CH_2$— group, the compound of the formula (II) can be prepared, for example, according to the Reaction Process 10:

Reaction Process 10

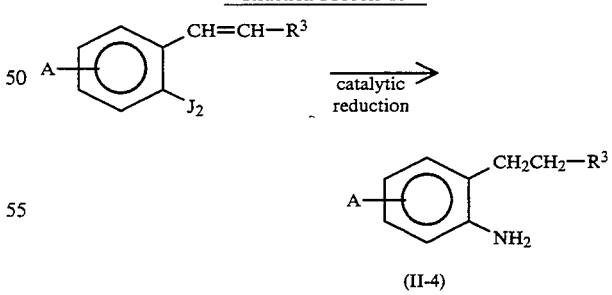

(II-4)

In the formula of the Reaction Process 10, $R^3$ and A are the same as defined above, and $J^2$ is a nitro group or an amino group.

(v) Where Z is a —C≡C— group, the compound of the formula (II) can be prepared, for example, according to the Reaction Process 11:

Reaction Process 11

(1)

-continued
Reaction Process 11

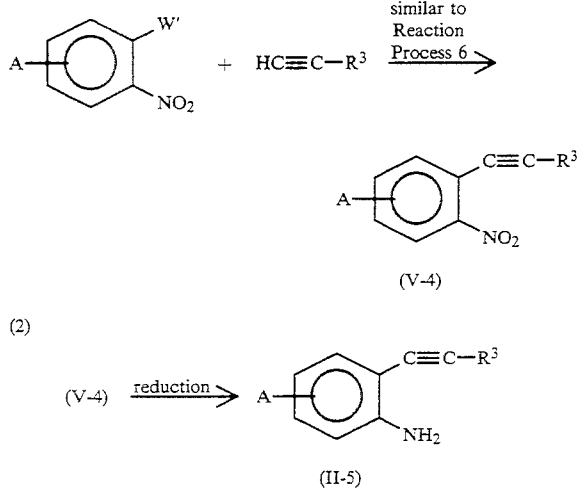

(V-4) $\xrightarrow{\text{reduction}}$

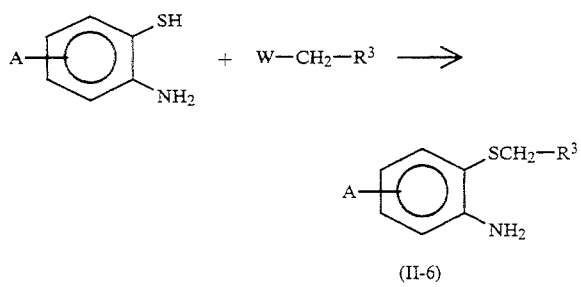

In the formula of the Reaction Process 11, A, W' and R³ are the same as defined above.

(vi) Where Z is a —SCH₂— group, the compound of the formula (II) can be prepared, for example, according to the following Reaction process 12:

Reaction Process 12

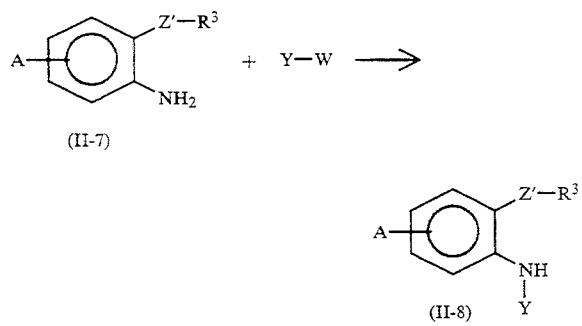

In the formula of the Reaction Process 12, A, W and R³ are the same as defined above.

The compound of the general formula (II) that is used in the Reaction Process 1 can be prepared, for example, according to the following Reaction process 13 in the case where R² in the formula (II) is Y as defined hereinbefore:

Reaction Process 13

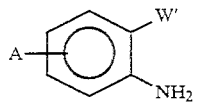

In the formula of the Reaction Process 13, A, Z', R³, Y and W are the same as defined above The compound represented by the general formula (III) that is used in the Reaction Process 2 can be prepared, for example, according to the following Reaction Process 14:

Reaction Process 14

(II-7) + phosgene → (III)

The compound represented by the general formula (IV) that is used in the- Reaction Process 5 can be prepared, for example, as follows.

(i) The compound of the formula (IV), where W is a chlorine atom or a bromine atom, can be prepared by reacting a derivative of 2-aminobenzyl alcohol with ClCO₂R¹ (wherein R¹ is the same as defined above) in a manner similar to that in Reaction Process 1 to form a compound represented by the following general formula:

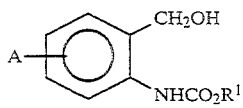

(wherein R¹ and A are the same as defined above) and subjecting the formed compound to customary chlorination, for example, with SOCl₂ or to customary bromination, for example, with SOBr₂.

(ii) The compound of the formula (IV), where W is an iodine atom, can be prepared by reacting, with an alkali metal iodide such as sodium iodide, the compound prepared in (i) above that is of the formula (IV) wherein W is a chlorine atom or a bromine atom.

The compound represented by the general formula (VI) that is used in the Reaction Process 6 can be prepared by reacting, with ClCO₂R¹ (R¹ is the same as defined above), a compound represented by the following general formula in a manner similar to that in the Reaction Process 1:

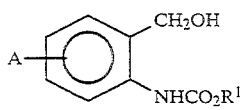

wherein A and W' are the same as defined above.

The compound of the general formula (II) can encompass its salts and geometrical isomers in some cases just like the compound of the general formula (I).

The Reaction Processes 1, 3, 5, 7 (1), 8 (1), 9 (1), 12 and 13 are usually effected in the presence of a solvent and a base. Examples of such a solvent include unsubstituted or substituted aromatic hydrocarbons such as benzene, toluene, xylene, and chlorobenz-ene; halogenated aliphatic hydrocarbons such as chloroform, carbon tetrachloride, methylene chloride, dichloroethane, trichloroethane; acyclic or cyclic aliphatic hydrocarbons such as n-hexane and cyclohexane; ethers such as diethyl ether, dioxane, and tetrahydrofuran; ketones such as acetone, methyl ethyl ketone, and methyl isobutyl ketone; nitriles such as acetonitrile and propionitrile; and aprotic polar solvents such as dimethylformamide, N-methyl-2-pyrrolidone, dimethylsulfoxide and sulfolane. As the base, either an inorganic base or an organic base can be used. Examples of such an inorganic base include alkali metal hydroxides such as sodium hydroxide and potassium hydroxides; alkali metal or alkaline earth metal carbonates such as anhydrous potassium carbonate and anhydrous calcium carbonate; alkali metal hydrides such as sodium hydride; and alkali metals such metallic sodium. Examples of such an organic base include pyridine and triethylamine. Particularly in the case where a —Z—R³ group is an unsubstituted or substituted a pyridylthiomethyl group, as well as in the case of the Reaction Process 9 (1), sodium hydride is preferably used as the base. The reaction temperature is usually in the range of −10° C. to +150° C. while the reaction time is usually in the range of 0.5 to 24 hours.

Additionally stated, in the case of the Reaction Processes 3 and 13, a catalyst such as tetrabutylammonium bromide may be used if necessary.

The Reaction Process 2 may be effected in the presence of a solvent and/or a catalyst if necessary. As the solvent, there can be mentioned those solvents as mentioned in connection with the Reaction Processes 1, 3, 5, 7 (1), 8 (1), 9 (1), 12 and 13. As the catalyst, there can be mentioned triethylamine, diethylaniline, 1,4-diazabicyclo(2. 2. 2)octane, etc. The reaction temperature is usually in the range of 0° to 50° C., while the reaction time is usually in the range of an instant to 10 hours.

m-Chloroperbenzoic acid and the like can be mentioned as the oxidizing agent to be used in the Reaction Process 4. A reaction of the compound represented by the general formula (I-4) with an equimolar amount of the oxidizing agent produces a compound with n=1 in the general formula (I-5). A reaction of the compound represented by the general formula (I-4) with a double-molar amount of the oxidizing agent produces a compound with n=2 in the general formula (I-5). The Reaction Process 4 may usually be carried out in the presence of an inactive solvent such as toluene, chloroform or methylene chloride at a temperature of 0° to 130° C. fro 0.1 to 24 hours.

Modes of the reduction reactions involved in the Reaction Processes 7 (2) and 8 (2) include catalytic reduction using a catalyst such as platinum oxide or palladium-carbon; reduction using a metal such as tin, iron or zinc together with an acid such as hydrochloric acid or sulfuric acid; and reduction suing an inorganic compound such as stannous chloride, ferrous sulfate, ferrous hydroxide or sodium sulfide, all of which are customarily practiced. In the case of reduction using an inorganic compound, the reduction may be effected in the presence of a mineral acid such as hydrochloric acid and in the presence of an alcohol such as ethanol if necessary.

Modes of the reduction reactions involved in the Reaction Processes 9 (2) and 11 (2) include the above-mentioned reduction using a metal together with an acid and the above-mentioned reduction using an inorganic compound except for the catalytic reduction. The Reaction Process 10 may be carried out by the above-mentioned catalytic reduction.

The Reaction Process 14 may be carried out in the presence of a solvent, examples of which include organic solvents such as benzene, toluene, xylene, and ethyl acetate. The reaction temperature may be in the range of 50° C. to reflux temperature, while the reaction time may be in the range of an instant to 10 hours.

The compound of the general formula (I) according to the present invention is useful as an active ingredient of biocidal compositions for control of harmful organisms. For example, the compound of the formula (I) can be used as the active ingredient of agricultural and horticultural fungicides to exhibit an excellent effect of controlling plant diseases such as rice blast, rice sheath blight, rice helminthosporium leaf spot, cucumber anthracnose, cucumber powdery mildew, cucumber downy mildew, tomato late blight, tomato early blight, citrus melanose, citrus common green mold, apple and pear scab, apple alternaria blotch, grape downy mildew, and gray mod, sclerotinia rot and rust of various crops; and soil diseases caused by phytopathogenic fungi such as Fusarium, Pythium, Rhizoctonia, Verticillium, and Plasmodiophora. The compound of the formula (I) exhibits an especially excellent effect of controlling rice blast, cucumber anthracnose, powdery mildew of various crops, gray mold of various crops, sclerotinia rot of various crops, rust of various crops, cucumber and grape downy mildew, and tomato and potato late blights. The compound of the present invention exhibits not only a long-term residual effect and an excellent preventive effect, but also has a curative effect to enable disease control to be effected through treatment therewith after infection. Furthermore, disease control is possible through soil treatment with the compound of the present invention. The compound of the present invention is effective not only against sensitive strains but also against various resistant strains such as Benomyl-resistant powdery mildew, Metalaxyl-resistant downy mildew, and Benomyl- and/or dicarboximide-resistant gray mold.

The compound of the present invention has a insecticidal, acaricidal and nematocidal activities as well and hence are effective against a variety of vermin in question.

The compound of the present invention may be used in combination with an adjuvant(s) to prepare various formulations such as an emulsifiable concentrate, a dust, a wettable powder, an aqueous solution, granules, a suspension concentrate, etc. like in the case of conventional agricultural chemical formulations. These formulations can be practically used either as such or after diluted with a diluent such as water to a predetermined concentration. As the adjuvant, there can be mentioned carriers, emulsifying agents, suspending agents, dispersants, spreaders, penetrating agents, wetting agents, thickening agents, and stabilizing agents, which may be appropriately added to the compound of the present invention as desired.

Carriers are classified into solid carriers and liquid carriers. Examples of solid carriers include animal or vegetable powders such as starch, sugar, cellulose powder, cyclodextrin, activated carbon, soybean powder, wheat powder, chaff powder, wood powder, fish powder, and powdery milk; and mineral powders such as talc, kaolin, bentonite, bentonite-alkylamine complex, calucium carbonate, calcium sulfate, sodium bicarbonate, zeolite, diatomaceous earth, white carbon, clay, alumina, silica, and sulfur powder. Examples of liquid carriers include water; animal or vegetable oils such as soybean oil, cotton seed oil, and corn oil; alcohols such as ethyl alcohol and ethylene glycol; ketones such as acetone and methyl ethyl ketone; ethers such as dioxane and tetrahydrofuran; aliphatic hydrocarbons such as kerosine, lamp oil, and liquid paraffin; aromatic hydrocarbons such as xylene, trimethylbenzene, tetramethylbenzene, cyclohexane, and solvent naphtha; halogenated hydrocarbons such as chloroform and chlorobenzene; acid amides such as dimethylformamide; esters such as ethyl acetate and fatty acid glycerin esters; nitriles such as acetonitrile; sulfur-containing compounds such as dimethylsulfoxide; and N-methylpyrrolidone.

The suitable blending weight ratio of the compound of the present invention to the adjuvant(s) is generally in the range of 0.05:99.95 to 90:10, and preferably in the range of 0.2:99.8 to 80:20.

The concentration of the compound of the present invention at the time of application varies depending on the crop as the object of application treatment, the way of application, the form of a formulation, the dose, etc., and hence cannot be generically determined. In the case of foliar appplication treatment, however, the concentration of the compound of the present invention as the active ingredient may usually be in the range of 0.1 to 10,000 ppm, and preferably in the range of 1 to 2,000 ppm. In the case of soil application treatment, the dose may usually be in the range of 10 to 100,000 g/ha (hectare), and preferably in the range of 200 to 20,000 g/ha.

A description will now be made of Formulation Examples of the biocidal composition of the present invention for control of harmful organisms, which comprises the compound of the present invention as the active ingredient. In the following Formulation Examples, Compounds Nos. are listed in Table 2 which will be given later.

| Formulation Example 1 | |
|---|---|
| (1) Compound No. 132 | 50 parts by weight |
| (2) kaolin | 40 parts by weight |
| (3) sodium lignosulfonate | 7 parts by weight |
| (4) a polyoxyethylene alkylphenyl ether | 3 parts by weight |

The above-mentioned components are uniformly mixed together to obtain a wettable powder.

| Formulation Example 2 | |
|---|---|
| (1) Compound No. 19 | 20 parts by weight |
| (2) white carbon | 10 parts by weight |
| (3) kaolin | 62 parts by weight |
| (4) sodium lignosulfonate | 4 parts by weight |
| (5) a polyoxyethylene alkylaryl ether | 4 parts by weight |

The above-mentioned components are uniformly mixed together to obtain a wettable powder.

| Formulation Example 3 | |
|---|---|
| (1) Compound No. 216 | 10 parts by weight |
| (2) diatomaceous earth | 15 parts by weight |
| (3) calcium carbonate powder | 69 parts by weight |
| (4) a dialkylsulfosuccinate | 1 part by weight |
| (5) a polyoxyethylene alkylphenyl ether sulfate | 3 parts by weight |
| (6) sodium β-naphthalenesulfonate-formalin condensate | 2 parts by weight |

The above-mentioned components are uniformly mixed together to obtain a wettable powder.

| Formulation Example 4 | |
|---|---|
| (1) Compound No. 52 | 6 parts by weight |
| (2) diatomaceous earth | 88 parts by weight |
| (3) a dialkylsulfosuccinate | 2 parts by weight |
| (4) a polyoxyethylene alkylphenyl ether sulfate | 4 parts by weight |

The above-mentioned components are uniformly mixed together to obtain a wettable powder.

| Formulation Example 5 | |
|---|---|
| (1) Compound No. 240 | 0.5 part by weight |
| (2) talc | 99.0 parts by weight |
| (3) phosphate of a lower alcohol | 0.5 part by weight |

The above-mentioned components are uniformly mixed together to obtain a dust.

| Formulation Example 6 | |
|---|---|
| (1) Compound No. 193 | 0.2 part by weight |
| (2) calcium carbonate powder | 98.8 parts by weight |
| (3) phosphate of a lower alcohol | 1 part by weight |

The above-mentioned components are uniformly mixed together to obtain a dust.

| Formulation Example 7 | |
|---|---|
| (1) Compound No. 224 | 20 parts by weight |
| (2) xylene | 60 parts by weight |
| (3) a polyoxyethylene alkylaryl ether | 20 parts by weight |

The above-mentioned components are mixed uniformly into solution to obtain an emulsifiable concentrate.

| Formulation Example 8 | |
|---|---|
| (1) Compound No. 57 | 1 part by weight |
| (2) bentonite | 33 parts by weight |
| (3) kaolin | 61 parts by weight |
| (4) sodium lignosulfonate | 5 parts by weight |

The above-mentioned components are admixed with a suitable amount of water for granulation and granulated to obtain granules.

| Formulation Example 9 | |
|---|---|
| (1) Compound No. 1 | 10 parts by weight |
| (2) corn oil | 77 parts by weight |
| (3) polyoxyethylene hydrogenated castor oil ether | 12 parts by weight |
| (4) a bentonite-alkylamine complex | 1 part by weight |

The above-mentioned components are mixed together and pulverized to obtain a suspension concentrate.

| Formulation Example 10 | |
|---|---|
| (1) Compound No. 19 | 10 parts by weight |
| (2) isoparaffin saturated hydrocarbons (fraction: 210–265° C.) | 79 parts by weight |
| (3) a mixture of a polyoxyethylene phenylphenol derivative and a polyoxyethylene sorbitan alkylate | 10 parts by weight |
| (4) a bentonite-alkylamine complex | 1 part by weight |

The above-mentioned components are mixed together and finely pulverized to obtain a suspension concentrate.

| Formulation Example 11 | |
|---|---|
| (1) Compound No. 159 | 40 parts by weight |
| (2) an oxyethylated polyaryl-phenol phosphate neutralized with triethanolamine | 2 parts by weight |
| (3) a silicone | 0.2 part by weight |
| (4) xanthan gum | 0.1 part by weight |
| (5) ethylene glycol | 5 parts by weight |
| (6) water | 52.7 parts by weight |

The above-mentioned components are uniformly mixed together and pulverized to obtain an aqueous suspension concentrate.

| Formulation Example 12 | |
|---|---|
| (1) Compound No. 138 | 75 parts by weight |
| (2) sodium polycarboxylate | 13.5 parts by weight |
| (3) anhydrous sodium sulfate | 10 parts by weight |
| (4) dextrin | 0.5 part by weight |
| (5) a sodium alkylsulfonate | 1 part by weight |

The above-mentioned components are placed in a high-speed mixing granulator, admixed with 20% water, granulated, and dried to obtain water-soluble granules.

If desired, the compound of the present invention may be used in mixture or combination with other agricultural chemical(s), examples of which include insecticides, acaricides, nematocides, fungicides, antiviral agents, attractants, herbicides, and plant growth regulators. In this case, the effect of the compound or biocidal composition of the present invention may sometimes be enhanced.

Specific examples of active ingredients of such insecticides, acaricides or nematocides include the following compounds:

Organic Phosphate Compounds
  O-(4-bromo-2-chlorophenyl) O-ethyl S-propyl phosphorothioate (common name: Profenofos),
  O-(2,2-dichlorovinyl) O,O-dimethylphosphate (common name: Dichlorvos),
  O-ethyl O-[3-methyl-4-(methylthio)phenyl]N-isopropyl phosphoroamidate (common name: Fenamiphos),
  O,O-dimethyl O-(4-nitro-m-tolyl) phosphorothioate (common name: Fenitrothion),
  O-ethyl O-(4-nitrophenyl)phenyl phosphonothioate (common name: EPN),
  O,O-diethyl O-(2-isopropyl-6-methylpyrimidin-4-yl) phosphorothioate (common name: Diazinon),
  O,O-dimethyl O-(3,5,6-trichloro-2-pyridyl)phosphorothioate (common name: Chlorpyrifos-methyl),
  O,S-dimethyl N-acetylphosphoramidothioate (common name: Acephate),
  O-(2,4-dichlorophenyl) O-ethyl S-propyl phosphorodithioate (common name: Prothiofos), and
  (RS)-S-sec-butyl O-ethyl 2-oxo-1,3-thiazolidin-3-yl phosphonothioate (disclosed in U.S. Pat. No. 4,590,182);

Carbamate Compounds
  1-naphthyl N-methylcarbamate (common name: Carbaryl),
  2-isopropoxyphenyl N-methylcarbamate (common name: Propoxur),
  2-methyl-2-(methylthio)propionaldehyde O-methylcarbamoyloxime (common name: Aldicarb),
  2,3-dihydro-2,2-dimethylbenzofuran-7-yl N-methylcarbamate (common name: Carbofuran),
  dimethyl N,N'-[thiobis[(methylimino)carbonyloxy]] bisethanimidothioate (common name: Thiodicarb),
  S-methyl N-(methylcarbamoyloxy)thioacetimidate (common name: Methomyl),
  N,N-dimethyl-2-methylcarbamoyloxyimino-2-(methylthio) acetamide (common name: Oxamyl),
  2-(ethylthiomethyl)phenyl N-methylcarbamate (common name: Ethiofencarb),
  2-dimethylamino-5,6-dimethylpyrimidin-4-yl N,N-dimethylcarbamate (common name: Pirimicarb), and
  2-sec-butylphenyl N-methylcarbamate (common name: Fenobucarb);

Nereistoxin Derivatives
  S,S'-2-dimethylaminotrimethylenebis(thiocarbamate) (common name: Cartap), and
  N,N-dimethyl-1,2,3-trithian-5-ylamine (common name: Thiocyclam);

Organic Chlorine Compounds
  2,2,2-trichloro-1,1-bis(4-chlorophenyl)ethanol (common name: Dicofol), and
  4-chlorophenyl-2,4,5-trichlorophenylsulfone (common name: Tetradifon);

Organometallic Compounds
  bis[tris(2-methyl-2-phenylpropyl)tin] oxide (common name: Fenbutatin Oxide);

Pyrethroid Compounds
  (RS)-α-cyano-3-phenoxybenzyl (RS)-2-(4-chlorophenyl)-3-methylbutylate (common name: Fenvalerate),
  3-phenoxybenzyl (1RS)-cis,trans-3-(2,2-dichlorovinyl)-2,2-dimethylcyclopropanecarboxylate (common name: Permethrin),
  (RS)-α-cyano-3-phenoxybenzyl (1RS)-cis,trans-3-(2,2-dichlorovinyl)-2,2-dimethylcyclopropanecarboxylate (common name: Cypermethrin),
  (S)-α-cyano-3-phenoxybenzyl (1R)-cis-3-(2,2-dibromovinyl)-2,2-dimethylcyclopropanecarboxylate (common name: Deltamethrin),
  (RS)-α-cyano-3-phenoxybenzyl (1RS)-cis,trans-3-(2-chloro-3,3,3-trifluoropropenyl)-2,2-dimethylcyclopropanecarboxylate (common name: Cyhalothrin),
  4-methyl-2,3,5,6-tetrafluorobenzyl-3-(2-chloro-3,3,3-trifluoro-1-propenyl)-2,2-dimethylcyclopropanecarboxylate (common name: Tefluthrin), and
  2-(4-ethoxyphenyl)-2-methylpropyl 3-phenoxybenzyl ether (common name: Ethofenprox);

Benzoylurea Compounds
  1-(4-chlorophenyl)-3-(2,6-difluorobenzoyl)urea (common name: Diflubenzuron),
  1-[3,5-dichloro-4-(3-chloro-5-trifluoromethyl-2-pyridyloxy)phenyl]-3-(2,6-difluorobenzoyl)urea (common name: Chlorfluazuron), and
  1-(3,5-dichloro-2,4-difluorophenyl)-3-(2,6-difluorobenzoyl)urea (common name: Teflubenzuron);

Juvenile Hormone-like Compounds
  isopropyl (2E,4E)-11-methoxy-3,7,11-trimethyl-2,4-dodecadienoate (common name: Methoprene);

Pyridazinone Compounds
  2-t-butyl-5-(4-t-butylbenzylthio)-4-chloro-3(2H) pyridazinone (common name: Pyridaben);

Pyrazole Compounds t-butyl 4-[(1,3-dimethyl-5-phenoxypyrazol-4-yl)methyleneamino-oxymethyl]benzoate (common name: Fenpyroximate);

Nitro Compounds 1-(6-chloro-3-pyridylmethyl)-N-nitro-imidazolidin-2-ylideneamine (common name: Imidacloprid), 1-[N-(6-chloro-3-pyridylmethyl)-N-ethylamino]-1-methylamino-2-nitroethylene (European Patent Laid-Open No. 302,389), 2-methylamino-2-[N-methyl-N-(6-chloro-3-pyridylmethyl)amino]-1-nitroethylene (European Patent Laid-Open No. 302,389), 1-(6-chloro-3-pyridylmethyl)amino-1-dimethylamino-2-nitroethylene (European Patent Laid-Open No. 302,389), 1-(6-chloro-3-pyridylmethyl)-2-(1-nitro-2-allylthioethylidene)imidazolidine (European Patent Laid-Open No. 437,784), 1-(6-chloro-3-pyridylmethyl)-2-(1-nitro-2-ethylthioethylidene)imidazolidine (European Patent Laid-Open No. 437,784), 1-(6-chloro-3-pyridylmethyl)-2-(1-nitro-2-$\beta$-methylallylthioethylidene)imidazolidine (European Patent Laid-Open No. 437,784), 1-(6-chloro-3-pyridylmethyl)-3-methyl-2-nitroguanidine (European Patent Laid-Open No. 383,091), 1-(6-chloro-3-pyridylmethyl)-3,3-dimethyl-2-nitroguanidine (European Patent Laid-Open No. 383,091), 3-(6-chloro-3-pyridylmethyl)-2-nitromethylenethiazolidine (European Patent Laid-Open No. 192,060), 1-(6-chloro-3-pyridylmethyl)-2-(nitromethylene)imidazolidine (European Patent Laid-Open No. 163,855), 6-(6-chloro-3-pyridylmethylamino)-1,3-dimethyl-5-nitro-1,2,3,4-tetrahydropyrimidine (European Patent Laid-Open No. 366,085), and 1-(6-chloro-3-pyridylmethyl)-5-nitro-3-methyl-6-methylamino-1,2,3,4-tetrahydropyrimidine (European Patent Laid-Open No. 366,085);

Dinitro Compounds Organic Sulfur Compounds Urea Compounds Triazine Compounds Hydrazine Compounds Other Compounds 2-tert-butylimino-3-isopropyl-5-phenyl-3,4,5,6-tetrahydro-2H-1,3,5-thiadiazin-4-one (common name: Buprofezin), trans-(4-chlorophenyl)-N-cyclohexyl-4-methyl-2-oxothiazolidinone-3-carboxamide (common name: Hexythiazox), N-methylbis(2,4-xylyliminomethyl)amine (common name: Amitraz), N'-(4-chloro-o-tolyl)-N,N-dimethylformamidine (common name: Chlordimeform), and (4-ethoxyphenyl)-[3-(4-fluoro-3-phenoxyphenyl)-propyl](dimethyl)silane (common name: Silafluofen).

The compound of the present invention may also be used in mixture or combination with microbial agricultural chemicals such as B.T. and insect viruses, and antibiotics such as avermectin and milbemycin.

Specific Examples of active ingredients of the aforementioned fungicides include the following compounds:

Pyrimidinamine Compounds 2-anilino-4-methyl-6-(1-propynyl)pyrimidine (disclosed in Japanese Patent Laid-Open No. 208,581/1988), Azole Compounds 1-(4-chlorophenoxy)-3,3-dimethyl-1-(1H-1,2,4-triazol-1-yl)butanone (common name: Triadimefon), 1-(biphenyl-4-yloxy)-3,3-dimethyl-1-(1H-1,2,4-triazol-1-yl)butan-2-ol (common name: Bitertanol), 1-[N-(4-chloro-2-trifluoromethylphenyl)-2-propoxyacetimidoyl]imidazole (common name: Triflumizole), 1-[2-(2,4-dichlorophenyl)-4-ethyl-1,3-dioxolan-2-ylmethyl]-1H-1,2,4-triazole (common name: Etaconazole)

1-[2-(2,4-dichlorophenyl)-4-propyl-1,3-dioxolan-2-ylmethyl]-1H-1,2,4-triazole (common name: propiconazole)

1-[2-(2,4-dichlorophenyl)pentyl]-1H-1,2,4-triazole (common name: Penconazole)

bis(4-fluorophenyl)(methyl)(1H-1,2,4-triazol-1-ylmethyl)silane (common name: Flusilazole), 2-(4-chlorophenyl)-2-(1H-1,2,4-triazol-1-yl-methyl)-hexanenitrile (common name: Myclobutanil), (2RS, 3RS)-2-(4-chlorophenyl)-3-cyclopropyl-1-(1H-1,2,4-triazol-1-yl)butan-2-ol (common name: Cyproconazole), (RS)-1-(4-chlorophenyl)-4,4-dimethyl-3-(1H-1,2,4-triazol-1-ylmethyl)pentan-3-ol (common name: Terbuconazole), (RS)-2(2,4-dichlorophenyl)-l(1H-1,2,4-triazol-1-yl)hexan-2-ol (common name: Hexaconazole), (2RS, 5RS)-5-(2,4-dichlorophenyl)tetrahydro-5-(1H-1,2,4-triazol-1-ylmethyl)-2-furyl 2,2,2-trifluoroethyl ether (common name: Furconazole-cis), and N-propyl-N-[2-(2,4,6-trichlorophenoxy)ethyl]imidazole-1-carboxamide (common name: Prochloraz);

Quinoxaline Compounds 6-methyl-1,3-dithiolo[4,5-b]quinoxalin-2-one (common name: Quinomethionate);

Dithiocarbamate Compounds manganese ethylenebis(dithiocarbamate) polymer (common name: Maneb), zinc ethylenebis(dithiocarbamate) polymer (common name: Zineb), complex of zinc with manganese ethylenebis(dithiocarbamate) (Maneb) (common name: Mancozeb), dizinc bis(dimethyldithiocarbamate) ethylenebis(dithiocarbamate) (common name: Polycarbamate), and zinc propylenebis(dithiocarbamate) polymer (common name: Propineb);

Organic Chlorine Compounds 4,5,6,7-tetrachlorophthalide (common name: Fthalide), tetrachloroisophthalonitrile (common name: Chlorothalonil), and pentachloronitrobenzene (common name: Quintozene);

Benzimidazole Compounds methyl 1-(butylcarbamoyl)benzimidazol-2-ylcarbamate (common name: Benomyl), dimethyl 4,4'-(o-phenylene)bis(3-thioallophanate) (common name: Thiophanate-Methyl), and methyl benzimidazol-2-ylcarbamate (common name: Carbendazim);

Pyridinamine Compounds 3-chloro-N-(3-chloro-2,6-dinitro-4-$\alpha,\alpha,\alpha$-trifluorotolyl)-5-trifluoromethyl-2-pyridinamine (common name: Fluazinam);

Cyanoacetamide Compounds
  1-(2-cyano-2-methoxyiminoacetyl)-3-ethylurea (common name: Cymoxanil);
Phenylamide compounds
  methyl N-(2-methoxyacetyl)-N-(2,6-xylyl)-DL-alaninate (common name: Metalaxyl),
  2-methoxy-N-(2-oxo-1,3-oxazolidin-3-yl)aceto-2',6'-xylidide (common name: Oxadixyl),
  (±)-α-2-chloro-N-(2,6-xylylacetamido)-γ-butyrolactone (common name: Ofurace),
  methyl N-phenylacetyl-N-(2,6-xylyl)-DL-alaninate (common name: Benalaxyl),
  methyl N-(2-furoyl)-N-(2,6-xylyl)-DL-alaninate (common name: Furalaxyl), and
  (±)-α-[N-(3-chlorophenyl)cyclopropanecarboxamido]-γ-butyrolactone (common name: Cyprofuram);
Sulfenic Acid Compounds
  N-dichlorofluoromethylthio-N', N'-dimethyl-N-phenylsulfamide (common name: Dichlofluanid);
Copper Compounds
  cupric hydroxide (common name: cupric hydroxide), and
  copper 8-quinolinolate (common name: Oxine-Copper);
Isoxazole Compounds
  5-methylisoxazol-3-ol (common name: Hydroxyisoxazole);
Organophosphorus Compounds
  aluminum tris(ethyl phosphonate) (common name: Fosetyl-Al),
  O-2,6-dichloro-p-tolyl-O,O-dimethyl phosphorothioate (common name: Tolcofos-methyl),
  S-benzyl O,O-diisopropyl phosphorothioate,
  O-ethyl S,S-diphenyl phosphorodithioate, and aluminum ethyl hydrogenphosphonate;
N-Halogenothioalkyl Compounds
  N-(trichloromethylthio)cyclohex-4-ene-1,2-dicarboximide (common name: Captan),
  N-(1,1,2,2-tetrachloroethylthio)cyclohex-4-ene-1,2-dicarboximide (common name: Captafol), and
  N-(trichloromethylthio)phthalimide (common name: Folpet);
Dicarboximide Compounds
  N-(3,5-dichlorophenyl)-1,2-dimethylcyclopropane-1,2-dicarboximide (common name: Procymidone),
  3-(3,5-dichlorophenyl)-N-isopropyl-2,4-dioxoimidazolidine-1-carboxamide (common name: Iprodione), and
  (RS)-3-(3,5-dichlorophenyl)-5-methyl-5-vinyl-1,3-oxazolidine-2,4-dione (common name: Vinclozolin);
Benzanilide Compounds
  α,α,α-trifluoro-3'-isopropoxy-o-toluanilide (common name: Flutolanil), and
  3'-isopropoxy-o-toluanilide (common name: Mepronil);
Benzamide Compounds
  2-(1,3-dimethylpyrazol-4-ylcarbonylamino)-4-methyl-3-pentenenitrile (disclosed in British Patent No. 2,190,375), and
  α-(nicotinylamino)-(3-fluorophenyl)acetonitrile (disclosed in Japanese Patent Laid Open No. 135,364/1988);
Piperazine Compounds
  N,N'-[piperazine-1,4-diylbis[trichloromethyl)methylene]]diformamide (common name: Triforine);
Pyridine Compounds
  2'4'-dichloro-2-(3-pyridyl)acetophenone O-methyloxime (common name: Pyrifenox);
Carbinol Compounds
  (±)-2,4'-dichloro-α-(pyrimidin-5-yl)benzhydryl alcohol (common name: Fenarimol), and
  (±)-2,4'-difluoro-α-(1H-1,2,4-triazol-1-yl-methyl)-benzhydryl alcohol (common name: Flutriafol);
Piperidine Compounds
  (RS)-1-[3-(4-tert-butylphenyl)-2-methylpropyl]-piperidine (common name: Fenpropidine);
Morpholine Compounds
  (±)-cis-4-[3-(4-tert-butylphenyl)-2-methylpropyl]-2,6-dimethylmorpholine (common name: Fenpropimorph);
Organotin Compounds
  triphenyltin hydroxide (common name: Fentin Hydroxide), and
  triphenyltin acetate (common name: Fentin Acetate);
Urea Compounds
  1-(4-chlorobenzyl)-1-cyclopentyl-3-phenylurea (common name: Pencycuron);
Cinnamic Acid Compounds
  (E,Z)4-[3-(4-chlorophenyl)-3-(3,4-dimethoxyphenyl)acryloyl]morpholine (common name: Dimethomorph);
Phenylcarbamate Compounds
  isopropyl 3,4-diethoxycarbanilate (common name: Diethofencarb);
Cyanopyrrole Compounds
  3-cyano-4-(2,2-difluoro-1,3-benzodioxol-4-yl)pyrrole (trade name: Saphire), and
  3-(2',3'-dichlorophenyl)-4-cyanopyrrole (common name: Fenpiclonil).

Other active ingredients of the fungicides include anthraquinone compounds, crotonic acid compounds and antibiotics.

The suitable blending weight ratio of the N-phenylcarbamate compound of the present invention represented by the general formula (I) to the other agricultural chemical(s) when used in mixture or combination may generally be in the range of 1:300 to 300:1, and preferably in the range of 1:100 to 100:1.

EXAMPLES

A description will now be made of specific Synthesis Examples of preparation of the compound of the present invention.

Synthesis Example 1

[Synthesis of methyl N-[2-(3-chloro-5-trifluoromethyl-2-pyridylthiomethyl)-phenyl]carbamate (Compound No. 1)]

[1] 2 g of 60 wt % sodium hydride were added to 45 ml of tetrahydrofuran under stirring at room temperature, followed by drop-wise addition thereto of a solution of 9.9 g of 3-chloro-2-mercapto-5-trifluoromethyl-pyridine in 40 ml of tetrahydrofuran. After completion of the drop-wise addition, the reaction mixture was heated under reflux for 30 minutes, and cooled to room temperature, followed by drop-wise addition thereto of a solution of 10 g of 2-nitrobenzyl bromide in 60 ml of tetrahydrofuran. After completion of the drop-wise addition, stirring was continued at room temperature for 15 hours. The reaction mixture was poured into water, subjected to extraction with ethyl acetate, washed with water, and dried over anhydrous sodium sulfate. The solvent was distilled off under reduced pressure. The resulting residue was purified by silica gel column chromatography (developing solvent:methylene chloride:hexane=4:1) to obtain 12 g of 2-(3-chloro-5-trifluoromethyl-2-pyridylthiomethyl)nitrobenzene.

[2] A mixture of 19.5 g of stannous chloride dihydrate and 28.5 ml of concentrated hydrochloric acid was cooled to 5° C. 10 g of 2-(3-chloro-5-trifluoromethyl-2-pyridylthiomethyl)nitrobenzene obtained in the step [1] was added to the cooled mixture at a stroke, followed by addition thereto of 52.5 ml of ethanol. The resulting mixture was gradually heated up to 80° C., at which heating was then continued for one hour. The reaction mixture was cooled, poured into water, and alkalized with a 40 wt % aqueous solution of potassium hydroxide. The precipitated solid was filtered off, and dried to obtain 8.3 g of 2-(3-chloro-5-trifluoromethyl-2-pyridylthiomethyl)aniline (Intermediate No. 1) having a melting point of 98° to 102° C.

[3] A solution of 2.23 g of 2-(3-chloro-5-trifluoromethyl-2-pyridylthiomethyl)aniline and 0.83 g of pyridine in 10 ml of toluene was drop-wise added to a solution of 1.1 g of methyl chloroformate in 10 ml of toluene under stirring at 10° to 15° C. After completion of the drop-wise addition, the reaction was continued at room temperature for 2 hours. After completion of the reaction, the reaction mixture was poured into water, subjected to extraction with ethyl acetate, washed with water, and dried over anhydrous sodium sulfate. The solvent was distilled off under reduced pressure. The resulting residue was washed with hexane. The precipitated solid was filtered off to obtain 1.9 g of the desired product (Compound No. 1) having a melting point of 111° to 113° C.

Synthesis Example 2

[Synthesis of methyl N-[2-(3-chloro-5-trifluoromethyl-2-pyridylthiomethyl)-phenyl]-N-(methoxymethyl)carbamate (Compound No. 3)]

0.22 g of potassium hydroxide powder was added little by little to a solution of 1 g of the compound obtained in the foregoing Synthesis Example 1 (Compound No. 1) in 12 ml of tetrahydrofuran, followed by addition thereto of 0.19 g of tetra-n-butylammonium bromide. 0.43 g of chloromethyl methyl ether was added to the resulting mixture at room temperature, at which stirring was then continued for 15 hours. The reaction mixture was poured into water, subjected to extraction with methylene chloride, washed with water, and dried over anhydrous sodium sulfate. The solvent was distilled off under reduced pressure. The resulting residue was purified by silica gel column chromatography (developing solvent:methylene chloride:hexane=1:1) to obtain 0.52 g of the desired product (Compound No. 3), which showed a refractive index $n_D^{26.4}$ of 1.5077.

Synthesis Example 3

[Synthesis of methyl N-[2-[[α-methyl-3-(trifluoromethyl)benzylidene]aminooxymethyl]phenyl]carbamate Compound No. 56)]

[1] 7.5 g of 3'-trifluoromethylacetophenone, 6.25 g of hydroxylamine hydrochloride, and 8.8 g of sodium acetate trihydrate were heated in 125 ml of methanol under reflux for one hour. After completion of the reaction, the methanol was distilled off under reduced pressure. 190 ml of water was added to the resulting residue, followed by extraction with ethyl acetate. The ethyl acetate layer was dried over anhydrous sodium sulfate and stripped of the solvent by distillation under reduced pressure to obtain 7.3 g of 3'-trifluoromethylacetophenone oxime having a melting point of 63° to 65° C.

[2] 0.66 g of 60 wt % sodium hydride was added to 18 ml of tetrahydrofuran under stirring at room temperature, followed by drop-wise addition thereto of a solution of 3 g of 3'-trifluoromethylacetophenone oxime obtained in the step [1] in 18 ml of tetrahydrofuran. After completion of the drop-wise addition, the reaction mixture was stirred at room temperature for one hour, followed by drop-wise addition thereto of a solution of 3 g of methyl N-[2-(chloromethyl)phenyl]carbamate in 20 ml of tetrahydrofuran. After completion of the drop-wise addition, stirring was continued at room temperature for 3 hours. The reaction mixture was poured into water, subjected to extraction with ethyl acetate, washed with water, and dried over anhydrous sodium sulfate. The solvent was distilled off under reduced pressure. The resulting residue was purified by silica gel column chromatography (developing solvent:methylene chloride:hexane=4:1) to obtain 1.8 g of the desired product (Compound No. 56) having a melting point of 77° to 80° C.

Synthesis Example 4

[Synthesis of methyl N-(methoxymethyl)-N-[2-[[α-methyl-3-(trifluoromethyl)benzylidene]aminooxymethyl]phenyl]carbamate (Compound No. 57)]

0.29 g of potassium hydroxide powder was added little by little to a solution of 1.3 g of the compound obtained in the foregoing Synthesis Example 3 (Compound No. 56) in 25 ml of tetrahydrofuran, followed by addition thereto of 0.25 of tetra-n-butylammonium bromide. 0.57 g of chloromethyl methyl ether was added to the resulting mixture at room temperature, at which stirring was then continued for one hour. The reaction mixture was poured into water, subjected to extraction with ether, washed with water, and dried over anhydrous sodium sulfate. The solvent was distilled off under reduced pressure. The resulting residue was purified by silica gel column chromatography (developing solvent:methylene chloride:hexane=3:1) to obtain 0.81 g of the desired product (Compound NO. 57), which showed a refractive index $n_D^{19.3}$ of 1.4761.

Synthesis Example 5

[Synthesis of methyl N-[2-(2-chlorostyryl)phenyl]carbamate (Compound No. 52)]

[1] 1.63 g of 60 wt % sodium hydride were added to 20 ml of tetrahydrofuran under stirring at room temperature, followed by cooling thereof to 0° C. and drop-wise addition thereto of a solution of 8 g of dimethyl 2-nitrobenzylphosphonate in 20 ml of tetrahydrofuran. After completion of the drop-wise addition, the reaction mixture was stirred at 0° C. for 30 minutes, followed by drop-wise addition thereto of 6.2 g of 2-chlorobenzaldehyde. After completion of the drop-wise addition, the resulting mixture was gradually heated up to room temperature, at which stirring was then continued for 17 hours. The reaction mixture was poured into water, subjected to extraction with ethyl acetate, washed with water, and dried over anhydrous sodium sulfate. The solvent was distilled off under reduced pressure. The resulting residue was purified twice by silica gel column chromatography (first developing solvent:methylene chloride:hexane=7:3, and second developing solvent:methylene chloride:hexane=3:1) to obtain 5.8 g of 2-chloro-2'-nitrostilbene.

[2] 23 ml of concentrated hydrochloric acid was added to 15.1 g of stannous chloride dihydrate to form a mixture, to which 5.8 g of 2-chloro-2'-nitrostilbene obtained in the step [1] and 41 ml of ethanol were added under stirring. Thereafter, the resulting mixture was gradually heated up to reflux temperature, at which heating was then continued for 25 minutes. The reaction mixture was cooled, poured into water, and alkalized with an aqueous solution of potassium hydroxide. The precipitated semisolid was filtered off. Ethyl acetate was added to the semisolid, followed by removal of insolubles through filtration. The filtrate was subjected to distillation under reduced pressure to obtain 5 g of oily 2-amino-2'-chlorostilbene (Intermediate No. 13).

[3] A solution of 5 g of 2-amino-2'-chlorostilbene obtained in the step [2] and 2.6 g of pyridine in 30 ml of toluene was drop-wise added to a solution of 3.4 g of methyl chloroformate in 39 ml of toluene under stirring at room temperature. After completion of the drop-wise addition, the reaction was continued at room temperature for 2 hours. After completion of the reaction, the reaction mixture was poured into water, subjected to extraction with ethyl acetate, washed with water, and dried over anhydrous sodium sulfate. The solvent was distilled off under reduced pressure. The resulting residue was purified twice by silica gel column chromatography (first developing solvent:methylene chloride:hexane=3:1, and second developing solvent:ethyl acetate:-hexane=1:4) to obtain 1.85 g of the desired product (Compound No. 52) having a melting point of 135° to 137° C.

Synthesis Example 6

[Synthesis of methyl N-[2-(2-chlorostyryl)phenyl]-N-(methoxymethyl)carbamate (Compound No. 53)]

0.29 g of potassium hydroxide powder was added little by little to a solution of 1 g of the compound obtained in the foregoing Synthesis Example 5 (Compound No. 52) in 20 ml of tetrahydrofuran, followed by addition thereto of 0.25 g of tetra-n-butylammonium bromide. 0.56 g of chloromethyl methyl ether was added to the resulting mixture at room temperature, at which stirring was then continued for one hour and 30 minutes. The reaction mixture was poured into water, subjected to extraction with ethyl acetate, washed with water, and dried over anhydrous sodium sulfate. The solvent was distilled off under reduced pressure. The resulting residue was purified by silica gel column chromatography (developing solvent:methylene chloride:-hexane=2:1) to obtain 0.54 g of the desired product in the form of a viscous liquid (Compound No. 53), the NMR data for which are listed in a description following Table 2 which will be given later.

Synthesis Example 7

[Synthesis of methyl N-[2-(3-chloro-5-trifluoromethyl-2-pyridylsulfinylmethyl)phenyl]carbamate (Compound No. 60)]

0.41 g of m-chloroperbenzoic acid was added little by little to a solution of 0.75 g of N-[2-(3-chloro-5-trifluoromethyl-2-pyridylthiomethyl)phenyl]carbamate obtained in the same manner as Synthesis Example 1 (Compound No. 1) in 20 ml of methylene chloride under stirring At room temperature. After completion of the addition, the reaction was continued at room temperature for 20 hours. The reaction mixture was poured into water, subjected to extraction with ethyl acetate, washed with water, and dried over anhydrous sodium sulfate. The solvent was distilled off under reduced pressure. The resulting residue was washed with hexane. The precipitated solid was filtered off to obtain 0.66 g of the desired product (Compound No. 60) having a melting point of 160° to 162° C.

Synthesis Example 8

[Synthesis of methyl N-[2-[[methylthio)(5-trifluoromethyl-2-pyridyl)methylene]aminooxymethyl]phenyl]carbamate (Compound No. 201)]

[1] 180 ml of ethanol were added to a solution of 22 g of 2-cyano-5-trifluoromethylpyridine in 180 ml of 1,2-dichloroethane under stirring at room temperature, followed by drop-wise addition thereto of a solution of 9.8 g of hydroxylamine hydrochloride in 17 ml of water. An aqueous solution of 5.6 g of sodium hydroxide in 17 ml of water was drop-wise added to the resulting mixture. After completion of the drop-wise addition, the reaction mixture was heated at 80° C. for 2 hours. The reaction mixture was cooled, and stripped of insolubles by filtration. The filtrate was subjected to distillation under reduced pressure to remove therefrom the solvent. The resulting residue was washed with hexane. The precipitated solid was filtered off to obtain 25 g of 5-trifluoromethyl-2-pyridinecarboxamide oxime having a melting point of 130° to 133° C.

[2] 10.25 g of 5-trifluoromethyl-2-pyridinecarboxamide oxime obtained in the foregoing step [1] were added to 175 ml of 4N hydrochloric acid under stirring. The resulting mixture was cooled to 0°-5° C., followed by drop-wise addition thereto of an aqueous solution of 4.15 g of sodium nitrite in 25 ml of water. After completion of the drop-wise addition, stirring was continued at 0°-5° C. for 3 hours. After completion of the reaction, the precipitated solid was filtered off to obtain 8.8 g of α-chloro-5-trifluoromethylpyridinecarbaldehyde oxime.

[3] 10 ml of a 15 wt % aqueous solution of sodium methanethiolate were drop-wise added to a solution of 4.49 g of α-chloro-5-trifluoromethylpyridinecarbaldehyde oxime obtained in the foregoing step [2] in 10 ml of tetrahydrofuran under stirring at room temperature. After completion of the drop-wise addition, stirring was continued at room temperature for one hour. After completion of the reaction, the reaction mixture was poured into water, subjected to extraction with ether, washed with water, and dried over anhydrous sodium sulfate. The solvent was distilled off under reduced pressure. The resulting residue was purified by silica gel column chromatography (developing solvent:methylene chloride) to obtain 3.5 g of α-methylthio-5-trifluoromethylpyridinecarbaldehyde oxime.

[4] 0.62 g of 60 wt % sodium hydride was added to 20 ml of tetrahydrofuran under stirring at room temperature, followed by drop-wise addition thereto of a solution of 3.3 g of α-methylthio-5-trifluoromethylpyridinecarbaldehyde oxime obtained in the foregoing step [3] in 30 ml of tetrahydrofuran. After completion of the drop-wise addition, the reaction mixture was stirred at room temperature for 30 minutes, followed by drop-wise addition thereto of a solution of 3.35 g of methyl N-[2-(chloromethyl)phenyl]carbamate in 30 ml of tetrahydrofuran. After completion of the drop-wise addition, stirring was continued at room temperature for 3 hours. The reaction mixture was poured into water, subjected to extraction with methylene chloride, washed with water, and dried over anhydrous sodium sulfate. The solvent was distilled off under reduced pressure. The resulting residue was purified by silica gel column chromatography (developing solvent:methylene chloride:hexane=1:2) to obtain 3.1 g of the desired product (Compound No. 201) having a melting point of 120° to 122° C.

Synthesis Example 9

[Synthesis of methyl N-(methoxymethyl)-N-[2[[methylthio)(5-trifluoromethyl-2-pyridyl)methylene]aminooxymethyl]phenyl]carbamate (Compound No. 202)]

0.28 g of potassium hydroxide powder was added little by little to a solution of 1.32 g of the compound obtained in the Synthesis Example 8 (Compound No. 201) in 25 ml of tetrahydrofuran, followed by addition thereto of 0.25 g of tetra-n-butylammonium bromide. 0.53 g of chloromethyl methyl ether was added to the resulting mixture at room temperature, at which stirring was then continued for one hour. The reaction mixture was poured into water, subjected to extraction with methylene chloride, washed with water, and dried over anhydrous sodium sulfate. The solvent was distilled off under reduced pressure. The resulting residue was purified by silica gel column chromatography (developing solvent:methylene chloride:hexane=1:2) to obtain 1.0 g of the desired product in the form of a semisolid (compound No. 202).

Synthesis Example 10

[Synthesis of methyl N-[2-[α-methylbenzylidene)aminooxymethyl]phenyl]carbamate (Compound No. 131)]

2.0 g of potassium hydroxide powder were added little by little to 30 ml of tetrahydrofuran, followed by drop-wise addition thereto, under stirring at room temperature, of a solution of 4.06 g of acetophenone oxime in 25 ml of tetrahydrofuran. After completion of the drop-wise addition, the reaction mixture was stirred at room temperature for 30 minutes, followed by drop-wise addition thereto of a solution of 6.0 g of methyl N-[2-(chloromethyl)phenyl]carbamate in 30 ml of tetrahydrofuran. After completion of the drop-wise addition, stirring was continued at room temperature for one hour and 20 minutes. The reaction mixture was poured into water, subjected to extraction with ethyl acetate, washed with water, and dried over anhydrous sodium sulfate. The solvent was distilled off under reduced pressure. The resulting residue was purified by silica gel column chromatography (developing solvent:methylene chloride:hexane=3:1) to obtain 5.7 g of the desired product (Compound No. 131) having a melting point of 84° to 88° C.

Synthesis Example 11

[Synthesis of methyl N-(methoxymethyl)-N-[2-[[α-methylbenzylidene)aminooxymethyl]phenyl]carbamate (Compound No. 132)]

0.82 g of potassium hydroxide powder was added little by little to a solution of 3.0 g of the compound obtained in the foregoing Synthesis Example 10 (Compound No. 131) in 50 ml of tetrahydrofuran, followed by addition thereto of 0.72 g of tetra-n-butylammonium bromide. 1.61 g of chloromethyl methyl ether were added to the resulting mixture at room temperature, at which stirring was then continued for 30 minutes. The reaction mixture was poured into water, subjected to extraction with ethyl acetate, washed With water, and dried over anhydrous sodium sulfate. The solvent was distilled off under reduced pressure. The resulting residue was purified by silica gel column chromatography (developing solvent: hexane: ethyl acetate=5: 1) to obtain 2.2 g of the desired product (Compound No. 132) having a melting point of 61° to 63° C., the NMR data for which are listed in a description following Table 2 which will be given layer.

Representative examples of the intermediate of the general formula (II) and the compound of the general formula (I) according to the present invention are listed in the following Table 1 and 2, respectively.

TABLE 1

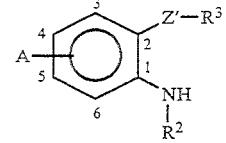

(II)

| Intermediate No. | $R^2$ | $Z'$ | $R^3$ | A | Physical Properties |
|---|---|---|---|---|---|
| 1 | H | —CH$_2$S— | 3-chloro-5-trifluoromethyl-2-pyridyl | H | m.p. 98–102° C. |
| 2 | H | —CH$_2$S— | 2-benzothiazolyl | H | — |
| 3 | H | —CH$_2$S— | 2-pyridyl | H | see NMR data mentioned later |
| 4 | H | —CH$_2$SCH$_2$— | phenyl | H | see NMR data mentioned later |
| 5 | H | —CH$_2$S— | 3-trifluoromethyl-2-pyridyl | H | see NMR data mentioned later |
| 6 | H | —CH$_2$S— | 5-trifluoromethyl-2-pyridyl | H | see NMR data mentioned later |
| 7 | H | —CH$_2$S— | 3,5-bis(trifluoromethyl)-2-pyridyl | H | — |
| 8 | H | —CH$_2$S— | 2-trifluoromethylphenyl | H | light yellow solid |
| 9 | H | —CH$_2$S— | 2-chlorophenyl | H | — |

TABLE 1-continued (II) Structure: benzene ring with positions 1-6, Z'—R³ at position 2, A at positions 4/5, NH-R² at position 1 (on position 6 adjacent).

| Intermediate No. | R² | Z' | R³ | A | Physical Properties |
|---|---|---|---|---|---|
| 10 | H | —CH₂S— | 3,5-dichloro-2-pyridyl | H | — |
| 11 | H | —SCH₂— | 2-chlorophenyl | H | see NMR data mentioned later |
| 12 | H | —SCH₂— | 3,5-dichloro-2-pyridyl | H | — |
| 13 | H | —CH=CH— | 2-chlorophenyl | H | oily substance |
| 14 | H | —CH₂S— | 5-chloro-1-methyl-2-benzimidazolyl and/or 5-chloro-3-methyl-2-benzimidazolyl | H | oily substance |
| 15 | H | —CH₂S— | 3-chloro-5-trifluoro-methyl-2-pyridyl | 6-CH₃ | m.p. 80–83° C. |
| 16 | H | —CH₂S— | 3-chloro-5-trifluoro-methyl-2-pyridyl | 5-Cl | m.p. 104–106° C. |
| 17 | H | —CH₂S— | 3-chloro-5-trifluoro-methyl-2-pyridyl | 4-CH₃ | — |
| 18 | H | —CH₂S— | 3-phenyl-5-trifluoro-methyl-2-pyridyl | H | m.p. 129–131° C. |
| 19 | H | —CH₂S— | 3-chloro-5-trifluoro-methyl-2-pyridyl | 4-OCH₃ | m.p. 93–95° C. |
| 20 | H | —CH₂S— | 3-chloro-5-trifluoro-methyl-2-pyridyl | 4-(3-chloro-5-trifluoro-methyl-2-pyridyl)oxy | m.p. 180–181° C. |
| 21 | H | —CH₂S— | 3-chloro-5-trifluoro-methyl-2-pyridyl | 6-OCH₃ | — |
| 22 | H | —CH₂S— | 3-chloro-5-trifluoro-methyl-2-pyridyl | 5-F | m.p. 130–133° C. |
| 23 | H | —CH₂S— | 3-chloro-5-trifluoro-methyl-2-pyridyl | 3-F | oily substance |

In Table 1, the hyphen on the right side of Z' represents a bond directed toward R³.

¹H-NMR data for intermediate No. 3 (in CDCl₃): 3.90–4.67 (br. s, 2H), 4.43 (s, 2H), 6.55–7.55 (m, 7H), 8.33–8.47 (dd, 1H)

¹H-NMR data for Intermediate No. 4 (in CDCl₃): 3.50–4.00 (br. s, 2H), 3.60 (s, 4H), 6.60–7.30 (m, 9H)

¹H-NMR data for Intermediate No. 5 (in CDCl₃): 3.97–4.40 (br. s, 2H), 4.50 (s, 2H), 6.57–7.27 (m, 5H), 7.80 (dd, 1H), 8.57 (dd, 1H)

¹H-NMR data for Intermediate No. 6 (in CDCl₃): 3.92–4.08 (br. s, 2H), 4.42 (s, 2H), 6.57–7.25 (m, 5H), 7.58 (dd, 1H), 8.67 (dd, 1H)

¹H-NMR data for Intermediate No. 11 (in CDCl₃): 3.97 (s, 2H), 4.07–4.43 (br. s, 2H), 6.40–7.37 (m, 8H)

TABLE 2

(I) Structure: benzene ring with Z—R³ at position 2, A at position 4/5, NCO₂R¹ with R² at position 1.

| Compound No. | R¹ | R² | Z | R³ | A | Physical Properties |
|---|---|---|---|---|---|---|
| 1 | —CH₃ | H | —CH₂S— | 3-chloro-5-trifluoro-methyl-2-pyridyl | H | m.p. 111–113° C. |
| 2 | —CH₃ | —CH₂CH₂CH₃ | —CH₂S— | 3-chloro-5-trifluoro-methyl-2-pyridyl | H | $n_D^{26.9}$1.4886 |
| 3 | —CH₃ | —CH₂OCH₃ | —CH₂S— | 3-chloro-5-trifluoro-methyl-2-pyridyl | H | $n_D^{26.4}$1.5077 |
| 4 | —CH₃ | —CH₃ | —CH₂S— | 3-chloro-5-trifluoro-methyl-2-pyridyl | H | viscous liquid |
| 5 | —CH₃ | —CH₂CH₃ | —CH₂S— | 3-chloro-5-trifluoro-methyl-2-pyridyl | H | $n_D^{24.2}$1.4708 |
| 6 | —CH₃ | —CH₂OCH₂CH₃ | —CH₂S— | 3-chloro-5-trifluoro-methyl-2-pyridyl | H | $n_D^{25}$1.5318 |
| 7 | —CH₃ | —CH₂CH=CH₂ | —CH₂S— | 3-chloro-5-trifluoro-methyl-2-pyridyl | H | $n_D^{25.1}$1.4826 |
| 8 | —CH₃ | —CO₂CH₃ | —CH₂S— | 3-chloro-5-trifluoro-methyl-2-pyridyl | H | m.p. 128–133° C. |
| 9 | —CH₃ | —CH₂CO₂CH₃ | —CH₂S— | 3-chloro-5-trifluoro-methyl-2-pyridyl | H | $n_D^{24.6}$1.4839 |

TABLE 2-continued

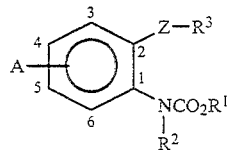

(I)

| Compound No. | R¹ | R² | Z | R³ | A | Physical Properties |
|---|---|---|---|---|---|---|
| 10 | —C₂H₅ | H | —CH₂S— | 3-chloro-5-trifluoro-methyl-2-pyridyl | H | m.p. 110–114° C. |
| 11 | —CH₃ | —CH₂C≡CH | —CH₂S— | 3-chloro-5-trifluoro-methyl-2-pyridyl | H | viscous liquid |
| 12 | -n-C₃H₇ | H | —CH₂S— | 3-chloro-5-trifluoro-methyl-2-pyridyl | H | m.p. 89–92° C. |
| 13 | -i-C₃H₇ | H | —CH₂S— | 3-chloro-5-trifluoro-methyl-2-pyridyl | H | m.p. 99–102° C. |
| 14 | —C₂H₅ | —CH₂OCH₃ | —CH₂S— | 3-chloro-5-trifluoro-methyl-2-pyridyl | H | $n_D^{22.1}$ 1.4771 |
| 15 | —CH₂CH₂Cl | H | —CH₂S— | 3-chloro-5-trifluoro-methyl-2-pyridyl | H | m.p. 79–81° C. |
| 16 | -n-C₄H₉ | H | —CH₂S— | 3-chloro-5-trifluoro-methyl-2-pyridyl | H | — |
| 17 | —CH₃ | —COCH₃ | —CH₂S— | 3-chloro-5-trifluoro-methyl-2-pyridyl | H | m.p. 87–88° C. |
| 18 | —CH₃ | —CH₂CH₂OCH₃ | —CH₂S— | 3-chloro-5-trifluoro-methyl-2-pyridyl | H | — |
| 19 | —CH₃ | H | —CH₂S— | 3,5-bis(trifluoro-methyl)-2-pyridyl | H | m.p. 109–113° C. |
| 20 | —CH₃ | —CH₂OCH₃ | —CH₂S— | 3,5-bis(trifluoro-methyl)-2-pyridyl | H | viscous liquid |
| 21 | —CH₃ | —CH₂C≡CH | —CH₂S— | 3,5-bis(trifluoro-methyl)-2-pyridyl | H | viscous liquid |
| 22 | —CH₃ | H | —CH₂S— | 3-trifluoromethyl-2-pyridyl | H | m.p. 97–105° C. |
| 23 | —CH₃ | —CH₂OCH₃ | —CH₂S— | 3-trifluoromethyl-2-pyridyl | H | $n_D^{20.5}$ 1.4850 |
| 24 | —CH₃ | H | —CH₂S— | 5-trifluoromethyl-2-pyridyl | H | m.p. 113–115° C. |
| 25 | —CH₃ | —CH₂OCH₃ | —CH₂S— | 5-trifluoromethyl-2-pyridyl | H | $n_D^{20.5}$ 1.4856 |
| 26 | —CH₃ | H | —CH₂S— | 3,5-dichloro-2-pyridyl | H | m.p. 112–115° C. |
| 27 | —CH₃ | —CH₂OCH₃ | —CH₂S— | 3,5-dichloro-2-pyridyl | H | viscous liquid |
| 28 | —CH₃ | H | —CH₂S— | 2-pyridyl | H | m.p. 65–67° C. |
| 29 | —CH₃ | —CH₂OCH₃ | —CH₂S— | 2-pyridyl | H | $n_D^{22.3}$ 1.4632 |
| 30 | —CH₃ | H | —CH₂S— | 2-chloro-4-trifluoro-methylphenyl | H | m.p. 147–149° C. |
| 31 | —CH₃ | —CH₂OCH₃ | —CH₂S— | 2-chloro-4-trifluoro-methylphenyl | H | m.p. 84–86° C. |
| 32 | —CH₃ | H | —CH₂S— | 2-chlorophenyl | H | m.p. 92–95° C. |
| 33 | —CH₃ | —CH₂OCH₃ | —CH₂S— | 2-chlorophenyl | H | $n_D^{16.7}$ 1.4699 |
| 34 | —CH₃ | H | —CH₂S— | 2-trifluoromethylphenyl | H | m.p. 106–108° C. |
| 35 | —CH₃ | —CH₂OCH₃ | —CH₂S— | 2-trifluoromethylphenyl | H | $n_D^{20.0}$ 1.4631 |
| 36 | —CH₃ | H | —CH₂S— | phenyl | H | $n_D^{23.9}$ 1.5391 |
| 37 | —CH₃ | —CH₂OCH₃ | —CH₂S— | phenyl | H | m.p. 70–72° C. |
| 38 | —CH₃ | H | —CH₂S— | 2-benzothiazolyl | H | m.p. 138–141° C. |
| 39 | —CH₃ | —CH₂CH₂CH₃ | —CH₂S— | 2-benzothiazolyl | H | m.p. 70–72° C. |
| 40 | —CH₃ | —CH₂OCH₃ | —CH₂S— | 2-benzothiazolyl | H | viscous liquid |
| 41 | —CH₃ | H | —SCH₂— | 3,5-dichloro-2-pyridyl | H | m.p. 47–49° C. |
| 42 | —CH₃ | —CH₂OCH₃ | —SCH₂— | 3,5-dichloro-2-pyridyl | H | $n_D^{17.5}$ 1.4882 |
| 43 | —CH₃ | H | —SCH₂— | 2-chlorophenyl | H | $n_D^{20.0}$ 1.4892 |
| 44 | —CH₃ | —CH₂OCH₃ | —SCH₂— | 2-chlorophenyl | H | viscous liquid |
| 45 | —CH₃ | H | —SCH₂— | phenyl | H | $n_D^{22.1}$ 1.4856 |
| 46 | —CH₃ | —CH₂OCH₃ | —SCH₂— | phenyl | H | m.p. 77–78° C. |
| 47 | —CH₃ | H | —CH₂O— | phenyl | H | $n_D^{25}$ 1.5244 |
| 48 | —CH₃ | —CH₂OCH₃ | —CH₂O— | phenyl | H | m.p. 78–81° C. |
| 49 | —CH₃ | H | —OCH₂— | phenyl | H | $n_D^{25.0}$ 1.5466 |
| 50 | —CH₃ | —CH₂OCH₃ | —OCH₂— | phenyl | H | $n_D^{25.0}$ 1.5364 |
| 51 | —CH₃ | —CH₂OCH₃ | —CH=CH— | phenyl | H | m.p. 85–88° C. |
| 52 | —CH₃ | H | —CH=CH— | 2-chlorophenyl | H | m.p. 135–137° C. |
| 53 | —CH₃ | —CH₂OCH₃ | —CH=CH— | 2-chlorophenyl | H | viscous liquid |
| 54 | —CH₃ | H | —CH₂SCH₂— | phenyl | H | m.p. 52–55° C. |
| 55 | —CH₃ | —CH₂OCH₃ | —CH₂SCH₂— | phenyl | H | $n_D^{22.0}$ 1.4768 |

TABLE 2-continued

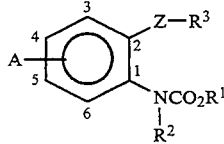

(I)

| Compound No. | $R^1$ | $R^2$ | Z | $R^3$ | A | Physical Properties |
|---|---|---|---|---|---|---|
| 56 | —$CH_3$ | H | —$CH_2$O—N=C(—$CH_3$)— | 3-trifluoromethylphenyl | H | m.p. 77–80° C. |
| 57 | —$CH_3$ | —$CH_2OCH_3$ | —$CH_2$O—N=C(—$CH_3$)— | 3-trifluoromethylphenyl | H | $n_D^{19.3}$1.4761 |
| 58 | —$CH_3$ | H | —$CH_2$O—N=CH— | 3-trifluoromethylphenyl | H | m.p. 57–61° C. |
| 59 | —$CH_3$ | —$CH_2OCH_3$ | —$CH_2$O—N=CH— | 3-trifluoromethylphenyl | H | $n_D^{17.3}$1.4939 |
| 60 | —$CH_3$ | H | —$CH_2$SO— | 3-chloro-5-trifluoromethyl-2-pyridyl | H | m.p. 160–162° C. |
| 61 | —$CH_3$ | H | —$CH_2SO_2$— | 3-chloro-5-trifluoromethyl-2-pyridyl | H | m.p. 182–184° C. |
| 62 | —$CH_3$ | H | —$CH_2$S— | 5-chloro-1-methyl-2-benzimidazolyl and/or 5-chloro-3-methyl-2-benzimidazolyl | H | m.p. 170–175° C. |
| 63 | —$CH_3$ | —$CH_2OCH_3$ | —$CH_2$S— | 5-chloro-1-methyl-2-benzimidazolyl and/or 5-chloro-3-methyl-2-benzimidazolyl | H | viscous liquid |
| 64 | —$CH_3$ | H | —$CH_2$O— | 2,4-dichlorophenyl | H | m.p. 111–112° C. |
| 65 | —$CH_3$ | H | —CH=CH— | 3-chloro-5-trifluoromethyl-2-pyridyl | H | — |
| 66 | —$CH_3$ | —$CH_2OCH_3$ | —CH=CH— | 3-chloro-5-trifluoromethyl-2-pyridyl | H | — |
| 67 | —$CH_3$ | —$CH_2CN$ | —$CH_2$S— | 3-chloro-5-trifluoromethyl-2-pyridyl | H | viscous liquid |
| 68 | —$CH_3$ | H | —$CH_2$O—N=C(—$CH_3$)— | 3-chloro-5-trifluoromethyl-2-pyridyl | H | — |
| 69 | —$CH_3$ | —$CH_2OCH_3$ | —$CH_2$O—N=C(—$CH_3$)— | 3-chloro-5-trifluoromethyl-2-pyridyl | H | — |
| 70 | —$CH_3$ | H | —$CH_2$O—N=CH— | 3-chloro-5-trifluoromethyl-2-pyridyl | H | — |
| 71 | —$CH_3$ | —$CH_2OCH_3$ | —$CH_2$O—N=CH— | 3-chloro-5-trifluoromethyl-2-pyridyl | H | — |
| 72 | —$CH_3$ | H | —$SCH_2$— | 3-chloro-5-trifluoromethyl-2-pyridyl | H | — |
| 73 | —$CH_3$ | —$CH_2OCH_3$ | —$SCH_2$— | 3-chloro-5-trifluoromethyl-2-pyridyl | H | — |
| 74 | —$CH_3$ | H | —$CH_2CH_2$— | 3-chloro-5-trifluoromethyl-2-pyridyl | H | — |
| 75 | —$CH_3$ | —$CH_2OCH_3$ | —$CH_2CH_2$— | 3-chloro-5-trifluoromethyl-2-pyridyl | H | — |
| 76 | —$CH_3$ | H | —C≡C— | 4-chlorophenyl | H | — |
| 77 | —$CH_3$ | —$CH_2OCH_3$ | —C≡C— | 4-chlorophenyl | H | — |
| 78 | —$CH_3$ | H | —$CH_2$S— | 2-benzoxazolyl | H | — |
| 79 | —$CH_3$ | —$CH_2OCH_3$ | —$CH_2$S— | 2-benzoxazolyl | H | — |
| 80 | —$CH_3$ | H | —$CH_2$S— | 1-methyl-5-trifluoromethylimidazo[5,4-a]-pyridin-2-yl | H | — |
| 81 | —$CH_3$ | —$CH_2OCH_3$ | —$CH_2$S— | 1-methyl-5-trifluoromethylimidazo[5,4-a]-pyridin-2-yl | H | — |
| 82 | —$CH_3$ | H | —CH=CH— | 2-pyridyl | H | m.p. 106–108° C. |
| 83 | —$CH_3$ | —$CH_2OCH_3$ | —CH=CH— | 2-pyridyl | H | m.p. 68–72° C. |
| 84 | —$CH_3$ | H | —$CH_2$O— | 5-chloro-2-benzoxazolyl | H | — |
| 85 | —$CH_3$ | —$CH_2OCH_3$ | —$CH_2$O— | 5-chloro-2-benzoxazolyl | H | — |

TABLE 2-continued $$\text{(I)}$$

Structure: benzene ring with positions 1-6; position 1 bears $NCO_2R^1$ and $R^2$ on N; position 2 bears $Z-R^3$; position 5 bears $A$.

| Compound No. | $R^1$ | $R^2$ | Z | $R^3$ | A | Physical Properties |
|---|---|---|---|---|---|---|
| 86 | —CH₃ | —CH₂—(cyclopropyl) | —CH₂S— | 3-chloro-5-trifluoromethyl-2-pyridyl | H | — |
| 87 | —CH₃ | —CH₂C≡C—I | —CH₂S— | 3-chloro-5-trifluoromethyl-2-pyridyl | H | — |
| 88 | —CH₂CF₃ | H | —CH₂S— | 3-chloro-5-trifluoromethyl-2-pyridyl | H | — |
| 89 | —CH₂CF₃ | —CH₂OCH₃ | —CH₂S— | 3-chloro-5-trifluoromethyl-2-pyridyl | H | — |
| 90 | —CH₃ | H | —CH₂S— | 3,5,6-trichloro-2-trifluoromethyl-4-pyridyl | H | — |
| 91 | —CH₃ | —CH₂OCH₃ | —CH₂S— | 3,5,6-trichloro-2-trifluoromethyl-4-pyridyl | H | — |
| 92 | —CH₃ | —CH₂SCH₃ | —CH₂S— | 3-chloro-5-trifluoromethyl-2-pyridyl | H | viscous liquid |
| 93 | —CH₃ | —CH(CH₃)—CO₂CH₃ | —CH₂S— | 3-chloro-5-trifluoromethyl-2-pyridyl | H | viscous liquid |
| 94 | —CH₃ | H | —CH₂S— | 3-chloro-5-trifluoromethyl-2-pyridyl | 6-CH₃ | m.p. 134–135° C. |
| 95 | —CH₃ | H | —CH₂S— | 3-chloro-5-trifluoromethyl-2-pyridyl | 4-CH₃ | m.p. 115–116° C. |
| 96 | —CH₃ | H | —CH₂S— | 3-chloro-5-trifluoromethyl-2-pyridyl | 5-Cl | m.p. 117–118° C. |
| 97 | —CH₃ | H | —CH₂S— | 3-phenyl-5-trifluoromethyl-2-pyridyl | H | m.p. 117–118° C. |
| 98 | —CH₃ | H | —CH₂S— | 2,3-(difluoromethylenedioxy)phenyl | H | m.p. 100–102° C. |
| 99 | —CH₃ | —CH₂OCH₃ | —CH₂S— | 2,3-(difluoromethylenedioxy)phenyl | H | viscous liquid |
| 100 | —CH₃ | H | —CH₂S— | 5-chloro-2-pyrimidinyl | H | m.p. 98–100° C. |
| 101 | —CH₃ | —CH₂OCH₃ | —CH₂S— | 5-chloro-2-pyrimidinyl | H | viscous liquid |
| 102 | —CH₃ | H | —CH₂O— | 1-pyrazolyl | H | m.p. 89–92° C. |
| 103 | —CH₃ | —CH₂C≡CH | —CH₂—O—N=C(CH₃)— | 3-trifluoromethylphenyl | H | viscous liquid |
| 104 | —CH₃ | H | —CH₂S— | 3-chloro-5-trifluoromethyl-2-pyridyl | 4-Cl | m.p. 134–136° C. |
| 105 | —CH₃ | —CH₂OCH₃ | —CH₂S— | 3-chloro-5-trifluoromethyl-2-pyridyl | 4-Cl | m.p. 106–108° C. |
| 106 | —CH₃ | H | —CH₂—O—N=C(CH₃)— | 2,4-dichlorophenyl | H | m.p. 128–132° C. |
| 107 | —CH₃ | —CH₂OCH₃ | —CH₂—O—N=C(CH₃)— | 2,4-dichlorophenyl | H | viscous liquid |
| 108 | —CH₃ | —CH₂C≡CH | —CH₂—O—N=C(CH₃)— | 2,4-dichlorophenyl | H | viscous liquid |
| 109 | —CH₃ | H | —CH₂—O—N=C(CH₃)— | 4-chlorophenyl | H | m.p. 127–130° C. |
| 110 | —CH₃ | —CH₂OCH₃ | —CH₂—O—N=C(CH₃)— | 4-chlorophenyl | H | viscous liquid |

TABLE 2-continued

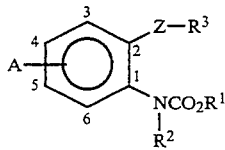
(I)

| Compound No. | $R^1$ | $R^2$ | Z | $R^3$ | A | Physical Properties |
|---|---|---|---|---|---|---|
| 111 | —$CH_3$ | —$CH_2C{\equiv}CH$ | —$CH_2O-N{=}C(CH_3)-$ | 4-chlorophenyl | H | viscous liquid |
| 112 | —$CH_3$ | H | —$CH_2S-$ | 5-chloro-3-trifluoromethyl-2-pyridyl | H | m.p. 111–112° C. |
| 113 | —$CH_3$ | —$CH_2OCH_3$ | —$CH_2S-$ | 5-chloro-3-trifluoromethyl-2-pyridyl | H | viscous liquid |
| 114 | —$CH_3$ | —$CH_2C{\equiv}CH$ | —$CH_2S-$ | 5-chloro-3-trifluoromethyl-2-pyridyl | H | viscous liquid |
| 115 | —$CH_3$ | H | —$CH_2S-$ | 4-methyl-5-phenyl-2-thiazolin-2-yl | H | viscous liquid |
| 116 | —$CH_3$ | —$CH_2OCH_3$ | —$CH_2S-$ | 4-methyl-5-phenyl-2-thiazolin-2-yl | H | viscous liquid |
| 117 | —$CH_3$ | H | —$CH_2S-$ | 4-methyl-5-phenyl-2-oxazolin-2-yl | H | viscous liquid |
| 118 | —$CH_3$ | —$CH_2OCH_3$ | —$CH_2S-$ | 4-methyl-5-phenyl-2-oxazolin-2-yl | H | viscous liquid |
| 119 | —$CH_3$ | H | —$CH_2O-N{=}C(CH_3)-$ | 3-trifluoromethylphenyl | 4-$CH_3$ | m.p. 87–89° C. |
| 120 | —$CH_3$ | —$CH_2OCH_3$ | —$CH_2O-N{=}C(CH_3)-$ | 3-trifluoromethylphenyl | 4-$CH_3$ | viscous liquid |
| 121 | —$CH_3$ | —$CH_2C{\equiv}CH$ | —$CH_2O-N{=}C(CH_3)-$ | 3-trifluoromethylphenyl | 4-$CH_3$ | viscous liquid |
| 122 | —$CH_3$ | H | —$CH_2S-$ | 3-chloro-5-trifluoromethyl-2-pyridyl | 4-$CH_3$ | viscous liquid |
| 123 | —$CH_3$ | —$CH_2OCH_3$ | —$CH_2S-$ | 3-chloro-5-trifluoromethyl-2-pyridyl | 4-$CH_3$ | viscous liquid |
| 124 | —$CH_3$ | —$COCH_3$ | —$CH_2S-$ | 3-chloro-5-trifluoromethyl-2-pyridyl | 4-$CH_3$ | m.p. 79–82° C. |
| 125 | —$CH_3$ | —$COCH_3$ | —$CH_2S-$ | 2-benzothiazolyl | H | m.p. 98–100° C. |
| 126 | —$CH_3$ | —$COCH_2Cl$ | —$CH_2S-$ | 3-chloro-5-trifluoromethyl-2-pyridyl | H | m.p. 112–115° C. |
| 127 | —$CH_3$ | —CO-cyclopropyl | —$CH_2S-$ | 3-chloro-5-trifluoromethyl-2-pyridyl | H | m.p. 107–108° C. |
| 128 | —$CH_3$ | —$COCH_2CH_3$ | —$CH_2S-$ | 3-chloro-5-trifluoromethyl-2-pyridyl | H | m.p. 96–99° C. |
| 129 | —$CH_3$ | —$COCH_3$ | —$CH_2O-N{=}C(CH_3)-$ | 3-trifluoromethylphenyl | H | m.p. 90–91° C. |
| 130 | —$CH_3$ | —$COCH(CH_3)_2$ | —$CH_2S-$ | 3-chloro-5-trifluoromethyl-2-pyridyl | H | m.p. 94–97° C. |
| 131 | —$CH_3$ | H | —$CH_2O-N{=}C(CH_3)-$ | phenyl | H | m.p. 84–88° C. |
| 132 | —$CH_3$ | —$CH_2OCH_3$ | —$CH_2O-N{=}C(CH_3)-$ | phenyl | H | m.p. 61–63° C. |

TABLE 2-continued $$\text{(I)}$$

Structure: benzene ring with positions 1-6; position 1 has $NCO_2R^1$ with $R^2$; position 2 has $Z-R^3$; position 4 (shown as 5 in diagram) has A.

| Compound No. | $R^1$ | $R^2$ | Z | $R^3$ | A | Physical Properties |
|---|---|---|---|---|---|---|
| 133 | $-CH_3$ | $-CH_2C{\equiv}CH$ | $-CH_2O-N{=}C(CH_3)-$ | phenyl | H | viscous liquid |
| 134 | $-CH_3$ | H | $-CH_2O-N{=}C(CH_3)-$ | 3-chlorophenyl | H | m.p. 120–122° C. |
| 135 | $-CH_3$ | $-CH_2OCH_3$ | $-CH_2O-N{=}C(CH_3)-$ | 3-chlorophenyl | H | viscous liquid |
| 136 | $-CH_3$ | $-CH_2C{\equiv}CH$ | $-CH_2O-N{=}C(CH_3)-$ | 3-chlorophenyl | H | viscous liquid |
| 137 | $-CH_3$ | H | $-CH_2O-N{=}C(CH_3)-$ | 3,5-bis(trifluoromethyl)phenyl | H | m.p. 117–120° C. |
| 138 | $-CH_3$ | $-CH_2OCH_3$ | $-CH_2O-N{=}C(CH_3)-$ | 3,5-bis(trifluoromethyl)phenyl | H | viscous liquid |
| 139 | $-CH_3$ | $-CH_2C{\equiv}CH$ | $-CH_2O-N{=}C(CH_3)-$ | 3,5-bis(trifluoromethyl)phenyl | H | viscous liquid |
| 140 | $-CH_3$ | $-CH_2C{\equiv}C-CH_3$ | $-CH_2S-$ | 3-chloro-5-trifluoromethyl-2-pyridyl | H | m.p. 96–97° C. |
| 141 | $-CH_3$ | $-CH_2C{\equiv}C-CH_3$ | $-CH_2O-N{=}C(CH_3)-$ | 3-trifluoromethylphenyl | H | viscous liquid |
| 142 | $-CH_3$ | $-CH_2C{\equiv}CCH_2CH_3$ | $-CH_2S-$ | 3-chloro-5-trifluoromethyl-2-pyridyl | H | viscous liquid |
| 143 | $-CH_3$ | H | $-CH_2O-N{=}C(CF_3)-$ | phenyl | H | m.p. 55–62° C. |
| 144 | $-CH_3$ | $-CH_2OCH_3$ | $-CH_2O-N{=}C(CF_3)-$ | phenyl | H | viscous liquid |
| 145 | $-CH_3$ | H | $-CH_2S-$ | 7-trifluoromethyl-4-quinolyl | H | m.p. 147–149° C. |
| 146 | $-CH_3$ | $-CH_2OCH_3$ | $-CH_2S-$ | 7-trifluoromethyl-4-quinolyl | H | m.p. 104–106° C. |
| 147 | $-CH_3$ | $-COCH_2OCH_3$ | $-CH_2S-$ | 3-chloro-5-trifluoromethylpyridyl | H | m.p. 92–94° C. |
| 148 | $-CH_3$ | H | $-CH_2O-$ | 3-methoxycarbonylphenyl | H | m.p. 85–87° C. |
| 149 | $-CH_3$ | H | $-CH_2O-N{=}C(CH_3)-$ | 4-bromophenyl | H | m.p. 125–127° C. |
| 150 | $-CH_3$ | $-CH_2OCH_3$ | $-CH_2O-N{=}C(CH_3)-$ | 4-bromophenyl | H | viscous liquid |
| 151 | $-CH_3$ | $-CH_2C{\equiv}CH$ | $-CH_2O-N{=}C(CH_3)-$ | 4-bromophenyl | H | viscous liquid |

TABLE 2-continued

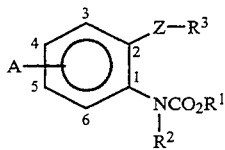
(I)

| Compound No. | R¹ | R² | Z | R³ | A | Physical Properties |
|---|---|---|---|---|---|---|
| 152 | —CH₃ | H | —CH₂O—N=C(CH₃)— | 4-trifluoromethylphenyl | H | m.p. 133–136° C. |
| 153 | —CH₃ | —CH₂OCH₃ | —CH₂O—N=C(CH₃)— | 4-trifluoromethylphenyl | H | m.p. 63–65° C. |
| 154 | —CH₃ | —CH₂C≡CH | —CH₂O—N=C(CH₃)— | 4-trifluoromethylphenyl | H | m.p. 66–69° C. |
| 155 | —CH₃ | H | —CH₂O—N=C(CH₃)— | 4-(3-chloro-5-trifluoromethyl-2-pyridyloxy)-phenyl | H | m.p. 92–94° C. |
| 156 | —CH₃ | H | —CH₂O—N=C(CH₃)— | 2-chlorophenyl | H | m.p. 101–103° C. |
| 157 | —CH₃ | —CH₂OCH₃ | —CH₂O—N=C(CH₃)— | 2-chlorophenyl | H | viscous liquid |
| 158 | —CH₃ | H | —CH₂O—N=C(CH₃)— | 5-chloro-2-pyridyl | H | m.p. 85–88° C. |
| 159 | —CH₃ | —CH₂OCH₃ | —CH₂O—N=C(CH₃)— | 5-chloro-2-pyridyl | H | viscous liquid |
| 160 | —CH₃ | —CH₂C≡CH | —CH₂O—N=C(CH₃)— | 5-chloro-2-pyridyl | H | viscous liquid |
| 161 | —CH₃ | H | —CH₂O—N=C(CH₃)— | 5-chloro-2-thienyl | H | m.p. 125–127° C. |
| 162 | —CH₃ | —CH₂OCH₃ | —CH₂O—N=C(CH₃)— | 5-chloro-2-thienyl | H | viscous liquid |
| 163 | —CH₃ | —CH₂C≡CH | —CH₂O—N=C(CH₃)— | 5-chloro-2-thienyl | H | m.p. 102–105° C. |
| 164 | —CH₃ | —CH₂C≡CCH₂CH₃ | —CH₂O—N=C(CH₃)— | 3-trifluoromethylphenyl | H | viscous liquid |
| 165 | —CH₃ | H | —CH₂O—N=C(CH₂CH₃)— | 3-chlorophenyl | H | m.p. 58–62° C. |
| 166 | —CH₃ | —CH₂OCH₃ | —CH₂O—N=C(CH₂CH₃)— | 3-chlorophenyl | H | viscous liquid |

TABLE 2-continued (I)

| Compound No. | R¹ | R² | Z | R³ | A | Physical Properties |
|---|---|---|---|---|---|---|
| 167 | —CH₃ | —CH₂C≡CH | —CH₂O—N=C(CH₂CH₃)— | 3-chlorophenyl | H | viscous liquid |
| 168 | —CH₃ | —CH₂-phenyl | —CH₂S— | 3-chloro-5-trifluoromethyl-2-pyridyl | H | viscous liquid |
| 169 | —CH₃ | —CH₂-phenyl | —CH₂O—N=C(CH₃)— | 3-trifluoromethylphenyl | H | viscous liquid |
| 170 | —CH₃ | H | —CH₂O—N=C(CH₃)— | 2-trifluoromethylphenyl | H | m.p. 38–40° C. |
| 171 | —CH₃ | —CH₂OCH₃ | —CH₂O—N=C(CH₃)— | 2-trifluoromethylphenyl | H | viscous liquid |
| 172 | —CH₃ | H | —CH₂O—N=C(CH₃)— | 4-methylphenyl | H | m.p. 79–81° C. |
| 173 | —CH₃ | H | —CH₂O—N=C(CH₃)— | 4-nitrophenyl | H | m.p. 170–172° C. |
| 174 | —CH₃ | —CH₂OCH₃ | —CH₂O—N=C(CH₃)— | 4-nitrophenyl | H | m.p. 72–74° C. |
| 175 | —CH₃ | H | —CH₂O—N=C(CH₃)— | 3,4-dichlorophenyl | H | m.p. 140–142° C. |
| 176 | —CH₃ | —CH₂OCH₃ | —CH₂O—N=C(CH₃)— | 3,4-dichlorophenyl | H | viscous liquid |
| 177 | —CH₃ | —CH₂C≡CH | —CH₂O—N=C(CH₃)— | 3,4-dichlorophenyl | H | viscous liquid |
| 178 | —CH₃ | H | —CH₂O—N=C(CO₂CH₃)— | phenyl | H | m.p. 98–100° C. |
| 179 | —CH₃ | H | —CH₂O—N=C(CO₂CH₃)— | 4-chlorophenyl | H | m.p. 116–118° C. |
| 180 | —CH₃ | H | —CH₂O—N=C(3-CF₃-phenyl)— | 3-trifluoromethylphenyl | H | viscous liquid |

TABLE 2-continued (I)

| Compound No. | R¹ | R² | Z | R³ | A | Physical Properties |
|---|---|---|---|---|---|---|
| 181 | —CH₃ | —CH₂OCH₃ | —CH₂O—N=C(3-CF₃-phenyl)— | 3-trifluoromethylphenyl | H | viscous liquid |
| 182 | —CH₃ | —CH₂C≡CH | —CH₂O—N=C(3-CF₃-phenyl)— | 3-trifluoromethylphenyl | H | viscous liquid |
| 183 | —CH₃ | H | —CH₂O— | 4-dimethylamino-3-methylphenyl | H | viscous liquid |
| 184 | —CH₃ | H | —CH₂S— | 3-chloro-5-trifluoromethyl-2-pyridyl | 6-OCH₃ | m.p. 123–125° C. |
| 185 | —CH₃ | —CH₂OCH₃ | —CH₂S— | 3-chloro-5-trifluoromethyl-2-pyridyl | 6-OCH₃ | m.p. 104–107° C. |
| 186 | —CH₃ | H | —CH₂S— | 3-chloro-5-trifluoromethyl-2-pyridyl | 4-(3-chloro-5-trifluoromethyl-2-pyridyl)oxy | m.p. 161–164° C. |
| 187 | —CH₃ | —CH₂CH₂F | —CH₂O—N=C(CH₃)— | 3-trifluoromethylphenyl | H | viscous liquid |
| 188 | —CH₃ | —CH₂CH₂F | —CH₂S— | 3-chloro-5-trifluoromethyl-2-pyridyl | H | viscous liquid |
| 189 | —CH₃ | H | —CH₂O—N=C(CH₃)— | 4-fluorophenyl | H | m.p. 133–135° C. |
| 190 | —CH₃ | —CH₂OCH₃ | —CH₂O—N=C(CH₃)— | 4-fluorophenyl | H | viscous liquid |
| 191 | —CH₃ | —CH₂C≡CH | —CH₂O—N=C(CH₃)— | 4-fluorophenyl | H | viscous liquid |
| 192 | —CH₃ | H | —CH₂O—N=C(CH₃)— | 3-methylphenyl | H | m.p. 76–78° C. |
| 193 | —CH₃ | —CH₂OCH₃ | —CH₂O—N=C(CH₃)— | 3-methylphenyl | H | viscous liquid |
| 194 | —CH₃ | —CH₂C≡CH | —CH₂O—N=C(CH₃)— | 3-methylphenyl | H | viscous liquid |
| 195 | —CH₃ | H | —CH₂O—N=C(CH₃)— | 3,5-dichlorophenyl | H | m.p. 152–155° C. |
| 196 | —CH₃ | —CH₂OCH₃ | —CH₂O—N=C(CH₃)— | 3,5-dichlorophenyl | H | viscous liquid |

TABLE 2-continued

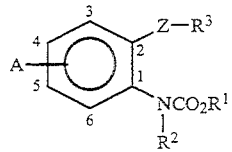

(I)

| Compound No. | R¹ | R² | Z | R³ | A | Physical Properties |
|---|---|---|---|---|---|---|
| 197 | —CH₃ | —CH₂C≡CH | —CH₂O—N=C(CH₃)— | 3,5-dichlorophenyl | H | viscous liquid |
| 198 | —CH₃ | H | —CH₂O—N=C(CH₃)— | 2-naphthyl | H | m.p. 95–98° C. |
| 199 | —CH₃ | —CH₂OCH₃ | —CH₂O—N=C(CH₃)— | 2-naphthyl | H | viscous liquid |
| 200 | —CH₃ | H | —CH₂O—N=C(CH₃)— | 2,3-(difluoromethyl-enedioxy)phenyl | H | m.p. 83–86° C. |
| 201 | —CH₃ | H | —CH₂O—N=C(SCH₃)— | 5-trifluoromethyl-2-pyridyl | H | m.p. 120–122° C. |
| 202 | —CH₃ | —CH₂OCH₃ | —CH₂O—N=C(SCH₃)— | 5-trifluoromethyl-2-pyridyl | H | semi-solid |
| 203 | —CH₃ | —CH₂C≡CH | —CH₂O—N=C(SCH₃)— | 5-trifluoromethyl-2-pyridyl | H | m.p. 100–102° C. |
| 204 | —CH₃ | H | —CH₂S— | 3-chloro-5-trifluoromethyl-2-pyridyl | 4-OCH₃ | m.p. 129–130° C. |
| 205 | —CH₃ | —CH₂OCH₃ | —CH₂S— | 3-chloro-5-trifluoromethyl-2-pyridyl | 4-OCH₃ | viscous liquid |
| 206 | —CH₃ | —CH₂C≡CH | —CH₂S— | 3-chloro-5-trifluoromethyl-2-pyridyl | 4-OCH₃ | viscous liquid |
| 207 | —CH₃ | H | —CH₂S— | 3-chloro-5-trifluoromethyl-2-pyridyl | 3-F | m.p. 115–117° C. |
| 208 | —CH₃ | —CH₂OCH₃ | —CH₂S— | 3-chloro-5-trifluoromethyl-2-pyridyl | 3-F | m.p. 90–91° C. |
| 209 | —CH₃ | —CH₂C≡CH | —CH₂S— | 3-chloro-5-trifluoromethyl-2-pyridyl | 3-F | viscous liquid |
| 210 | —CH₃ | H | —CH₂S— | 3-chloro-5-trifluoromethyl-2-pyridyl | 5-F | m.p. 124–127° C. |
| 211 | —CH₃ | —CH₂OCH₃ | —CH₂S— | 3-chloro-5-trifluoromethyl-2-pyridyl | 5-F | viscous liquid |
| 212 | —CH₃ | —CH₂C≡CH | —CH₂S— | 3-chloro-5-trifluoromethyl-2-pyridyl | 5-F | viscous liquid |
| 213 | —CH₃ | —CH₂OCH₃ | —CH₂S— | 3-chloro-5-trifluoromethyl-2-pyridyl | 4-(3-chloro-5-trifluoromethyl-2-pyridyl)oxy | viscous liquid |
| 214 | —CH₃ | H | —CH₂O—N=C(CH₃)— | 3-trifluoromethanesulfonyloxyphenyl | H | m.p. 68–70° C. |
| 215 | —CH₃ | —CH₂OCH₃ | —CH₂O—N=C(CH₃)— | 3-trifluoromethanesulfonyloxyphenyl | H | viscous liquid |
| 216 | —CH₃ | H | —CH₂O—N=C(CH₃)— | 3-methoxyphenyl | H | m.p. 80–85° C. |
| 217 | —CH₃ | —CH₂OCH₃ | —CH₂O—N=C(CH₃)— | 3-methoxyphenyl | H | viscous liquid |

TABLE 2-continued (I) Structure: benzene ring with positions 1-6; position 1 has NCO₂R¹ with R² substituent; position 2 has Z—R³; position 4 has A.

| Compound No. | R¹ | R² | Z | R³ | A | Physical Properties |
|---|---|---|---|---|---|---|
| 218 | —CH₃ | H | —CH₂O—N=C(CH₃)— | 4-chloro-3-trifluoromethylphenyl | H | m.p. 86–90° C. |
| 219 | —CH₃ | H | —CH₂O— | 3-methoxyiminomethylphenyl | H | m.p. 103–104° C. |
| 220 | —CH₃ | —CH₂OCH₃ | —CH₂O— | 3-methoxyiminomethylphenyl | H | viscous liquid |
| 221 | —CH₃ | H | —CH₂O— | 3-(l-methoxyimino)ethylphenyl | H | m.p. 90–91° C. |
| 222 | —CH₃ | —CH₂OCH₃ | —CH₂O— | 3-(l-methoxyimino)ethylphenyl | H | viscous liquid |
| 223 | —CH₃ | H | —CH₂O—N=C(CH₃)— | 3,4-methylenedioxyphenyl | H | m.p. 117–119° C. |
| 224 | —CH₃ | —CH₂OCH₃ | —CH₂O—N=C(CH₃)— | 3,4-methylenedioxyphenyl | H | viscous liquid |
| 225 | —CH₃ | —CH₂OCH₃ | —CH₂O—N=C(CH₃)— | 2,3-(difluoromethylenedioxy)phenyl | H | viscous liquid |
| 226 | —CH₃ | H | —CH₂O—N=C(CH₃)— | 3,4-ethylenedioxyphenyl | H | m.p. 97–101° C. |
| 227 | —CH₃ | —CH₂OCH₃ | —CH₂O—N=C(CH₃)— | 3,4-ethylenedioxyphenyl | H | viscous liquid |
| 228 | —CH₃ | H | —CH₂O—N=C(CH₃)— | 3-methylphenyl | 4-CH₃ | m.p. 83–85° C. |
| 229 | —CH₃ | —CH₂OCH₃ | —CH₂O—N=C(CH₃)— | 3-methylphenyl | 4-CH₃ | viscous liquid |
| 230 | —CH₃ | —CH₂C≡CH | —CH₂O—N=C(CH₃)— | 3-methylphenyl | 4-CH₃ | viscous liquid |
| 231 | —CH₃ | H | —CH₂O—N=C(CN)— | 3-trifluoromethylphenyl | H | m.p. 137–139° C. |
| 232 | —CH₃ | —CH₂OCH₃ | —CH₂O—N=C(CN)— | 3-trifluoromethylphenyl | H | m.p. 79–81° C. |
| 233 | —CH₃ | H | —CH₂O—N=C(NH₂)— | 5-trifluoromethyl-2-pyridyl | H | m.p. 116–118° C. |
| 234 | —CH₃ | H | —CH₂O—N=C(morpholino)— | 3-trifluoromethylphenyl | H | viscous liquid |

TABLE 2-continued

Structure (I):

Phenyl ring with positions 1-6; position 1 bears N(R²)CO₂R¹; position 2 bears Z—R³; position 4 bears A.

| Compound No. | R¹ | R² | Z | R³ | A | Physical Properties |
|---|---|---|---|---|---|---|
| 235 | —CH₃ | H | —CH₂O—N=C(cyclopropyl)— | 4-chlorophenyl | H | m.p. 69–74° C. |
| 236 | —CH₃ | —CH₂OCH₃ | —CH₂O—N=C(cyclopropyl)— | 4-chlorophenyl | H | viscous liquid |
| 237 | —CH₃ | H | —CH₂O—N=C(CH₃)— | 3-bromophenyl | H | m.p. 124–126° C. |
| 238 | —CH₃ | —CH₂OCH₃ | —CH₂O—N=C(CH₃)— | 3-bromophenyl | H | viscous liquid |
| 239 | —CH₃ | H | —CH₂O—N=C(CH₃)— | 2-pyridyl | H | m.p. 93–95° C. |
| 240 | —CH₃ | —CH₂OCH₃ | —CH₂O—N=C(CH₃)— | 2-pyridyl | H | viscous liquid |
| 241 | —CH₃ | H | —CH₂O—N=C(CH₃)— | 3-pyridyl | H | m.p. 88–90° C. |
| 242 | —CH₃ | —CH₂OCH₃ | —CH₂O—N=C(CH₃)— | 3-pyridyl | H | viscous liquid |
| 243 | —CH₃ | H | —CH₂O—N=C(CH₃)— | 3-(difluoromethoxy)-phenyl | H | m.p. 89–91° C. |
| 244 | —CH₃ | —CH₂OCH₃ | —CH₂O—N=C(CH₃)— | 3-(difluoromethoxy)-phenyl | H | viscous liquid |
| 245 | —CH₃ | H | —CH₂O—N=C(CH₃)— | 2-thienyl | H | m.p. 106–108° C. |
| 246 | —CH₃ | —CH₂OCH₃ | —CH₂O—N=C(CH₃)— | 2-thienyl | H | viscous liquid |
| 247 | —CH₃ | H | —CH₂O—N=C(CH₃)— | phenyl | 4-CH₃ | m.p. 89–91° C. |
| 248 | —CH₃ | —CH₂OCH₃ | —CH₂O—N=C(CH₃)— | phenyl | 4-CH₃ | viscous liquid |
| 249 | —CH₃ | H | —CH₂O—N=C(CH₃)— | 3-fluorophenyl | H | m.p. 115–118° C. |
| 250 | —CH₃ | —CH₂OCH₃ | —CH₂O—N=C(CH₃)— | 3-fluorophenyl | H | viscous liquid |

TABLE 2-continued

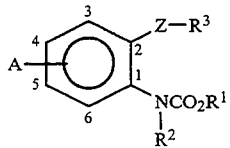
(I)

| Compound No. | R¹ | R² | Z | R³ | A | Physical Properties |
|---|---|---|---|---|---|---|
| 251 | —CH₃ | —CH₂CH=CH₂ | —CH₂O—N=C(CH₃)— | 3-trifluoromethyl-phenyl | H | viscous liquid |
| 252 | —CH₃ | —CH₂CH₃ | —CH₂O—N=C(CH₃)— | 3-trifluoromethyl-phenyl | H | viscous liquid |
| 253 | —CH₃ | H | —CH₂O—N=C(H)— | phenyl | H | m.p. 55–57° C. |
| 254 | —CH₃ | —CH₂OCH₃ | —CH₂O—N=C(H)— | phenyl | H | viscous liquid |
| 255 | —CH₃ | H | —CH₂O—N=C(CH₂CH₃)— | phenyl | H | viscous liquid |
| 256 | —CH₃ | —CH₂OCH₃ | —CH₂O—N=C(CH₂CH₃)— | phenyl | H | viscous liquid |
| 257 | —CH₃ | H | —CH₂O—N=C(CH₃)— | 2-furyl | H | m.p. 78–80° C. |
| 258 | —CH₃ | —CH₂OCH₃ | —CH₂O—N=C(CH₃)— | 2-furyl | H | viscous liquid |
| 259 | —CH₃ | H | —CH₂O—N=C(SCH₃)— | 2-pyridyl | H | m.p. 118–119° C. |
| 260 | —CH₃ | —CH₂OCH₃ | —CH₂O—N=C(SCH₃)— | 2-pyridyl | H | viscous liquid |
| 261 | —CH₃ | H | —CH₂O—N=C(CH₃)— | 1-methyl-3-indolyl | H | m.p. 150–152° C. |
| 262 | —CH₃ | —CH₂OCH₃ | —CH₂O—N=C(CH₃)— | 4-methylphenyl | H | — |
| 263 | —CH₃ | H | —CH₂O—N=C(CH₃)— | 1-methyl-3-pyrrolyl | H | m.p. 128–130° C. |
| 264 | —CH₃ | —CH₂OCH₃ | —CH₂O—N=C(CH₃)— | 1-methyl-3-pyrrolyl | H | viscous liquid |
| 265 | —CH₃ | H | —CH₂O—N=C(CH₃)— | 4-(methylthio)phenyl | H | m.p. 88–92° C. |

TABLE 2-continued

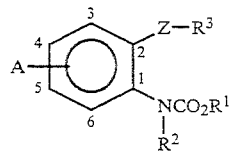
(I)

| Compound No. | $R^1$ | $R^2$ | Z | $R^3$ | A | Physical Properties |
|---|---|---|---|---|---|---|
| 266 | —$CH_3$ | —$CH_2OCH_3$ | —$CH_2O$—N=C(—$CH_3$)— | 4-(methylthio)phenyl | H | viscous liquid |
| 267 | —$CH_3$ | H | —$CH_2O$—N=C(—$SCH_3$)— | phenyl | H | — |
| 268 | —$CH_3$ | —$CH_2OCH_3$ | —$CH_2O$—N=C(—$SCH_3$)— | phenyl | H | — |
| 269 | —$CH_3$ | H | —$CH_2O$—N=C(—$CH_3$)— | 3-acetyloxyphenyl | H | — |
| 270 | —$CH_3$ | —$CH_2OCH_3$ | —$CH_2O$—N=C(—$CH_3$)— | 3-acetyloxyphenyl | H | — |
| 271 | —$CH_3$ | H | —$CH_2O$—N=C(—$CH_3$)— | 3-(2-tetrahydropyranyl)oxyphenyl | H | — |
| 272 | —$CH_3$ | —$CH_2OCH_3$ | —$CH_2O$—N=C(—$CH_3$)— | 3-(2-tetrahydropyranyl)oxyphenyl | H | — |
| 273 | —$CH_3$ | H | —$CH_2O$—N=C(—$CH_3$)— | 3-(dimethylcarbamoyl)oxyphenyl | H | viscous liquid |
| 274 | —$CH_3$ | —$CH_2OCH_3$ | —$CH_2O$—N=C(—$CH_3$)— | 3-(dimethylcarbamoyl)oxyphenyl | H | viscous liquid |
| 275 | —$CH_3$ | H | —$CH_2O$—N=C(—$CH_3$)— | 3-cyanophenyl | H | m.p. 148–150° C. |
| 276 | —$CH_3$ | —$CH_2OCH_3$ | —$CH_2O$—N=C(—$CH_3$)— | 3-cyanophenyl | H | viscous liquid |
| 277 | —$CH_3$ | H | —$CH_2O$—N=C(—$CH_3$)— | 3-dimethylaminophenyl | H | m.p. 109–111° C. |
| 278 | —$CH_3$ | —$CH_2OCH_3$ | —$CH_2O$—N=C(—$CH_3$)— | 3-dimethylaminophenyl | H | viscous liquid |
| 279 | —$CH_3$ | H | —$CH_2O$—N=C(—$CH_3$)— | 3-biphenylyl | H | viscous liquid |
| 280 | —$CH_3$ | —$CH_2OCH_3$ | —$CH_2O$—N=C(—$CH_3$)— | 3-biphenylyl | H | viscous liquid |
| 281 | —$CH_3$ | H | —$CH_2O$—N=C(—$CH_3$)— | 4-methoxyphenyl | H | m.p. 109–111° C. |

TABLE 2-continued

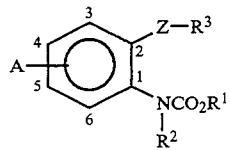

(I)

| Compound No. | $R^1$ | $R^2$ | Z | $R^3$ | A | Physical Properties |
|---|---|---|---|---|---|---|
| 282 | —CH$_3$ | —CH$_2$OCH$_3$ | —CH$_2$O—N=C(CH$_3$)— | 4-methoxyphenyl | H | viscous liquid |
| 283 | —CH$_3$ | H | —CH$_2$O—N=C(CH$_3$)— | 3,4-dimethoxyphenyl | H | m.p. 159–161° C. |
| 284 | —CH$_3$ | —CH$_2$OCH$_3$ | —CH$_2$O—N=C(CH$_3$)— | 3,4-dimethoxyphenyl | H | viscous liquid |
| 285 | —CH$_3$ | H | —CH$_2$O—N=C(CH$_3$)— | 2,4-dimethoxyphenyl | H | m.p. 120–122° C. |
| 286 | —CH$_3$ | —CH$_2$OCH$_3$ | —CH$_2$O—N=C(CH$_3$)— | 2,4-dimethoxyphenyl | H | viscous liquid |
| 287 | —CH$_3$ | H | —CH$_2$O—N=C(CH$_3$)— | 2,5-dimethoxyphenyl | H | m.p. 45–47° C. |
| 288 | —CH$_3$ | —CH$_2$OCH$_3$ | —CH$_2$O—N=C(CH$_3$)— | 2,5-dimethoxyphenyl | H | viscous liquid |
| 289 | —CH$_3$ | H | —CH$_2$O—N=C(CH$_3$)— | 3-ethoxyphenyl | H | m.p. 96–98° C. |
| 290 | —CH$_3$ | —CH$_2$OCH$_3$ | —CH$_2$O—N=C(CH$_3$)— | 3-ethoxyphenyl | H | viscous liquid |
| 291 | —CH$_3$ | H | —CH$_2$O—N=C(CH$_3$)— | 3-(methoxymethyl)-phenyl | H | — |
| 292 | —CH$_3$ | —CH$_2$OCH$_3$ | —CH$_2$O—N=C(CH$_3$)— | 3-(methoxymethyl)-phenyl | H | — |
| 293 | —CH$_3$ | H | —CH$_2$O—N=C(CH$_3$)— | 2-pyrazinyl | H | — |
| 294 | —CH$_3$ | —CH$_2$OCH$_3$ | —CH$_2$O—N=C(CH$_3$)— | 2-pyrazinyl | H | — |
| 295 | —CH$_3$ | H | —CH$_2$O—N=C(CH$_3$)— | 2,4-dimethyl-5-thiazolyl | H | — |
| 296 | —CH$_3$ | —CH$_2$OCH$_3$ | —CH$_2$O—N=C(CH$_3$)— | 2,4-dimethyl-5-thiazolyl | H | — |
| 297 | —CH$_3$ | H | —CH$_2$O—N=C(CH$_3$)— | 2,4-dimethyl-5-oxazolyl | H | — |

TABLE 2-continued (I)

Structure: benzene ring with positions labeled, substituent $Z-R^3$ at position 2, $A$ at position 4-5, $N(R^2)CO_2R^1$ at position 1.

| Compound No. | $R^1$ | $R^2$ | Z | $R^3$ | A | Physical Properties |
|---|---|---|---|---|---|---|
| 298 | —$CH_3$ | —$CH_2OCH_3$ | —$CH_2O$—N=C(—$CH_3$)— | 2,4-dimethyl-5-oxazolyl | H | — |
| 299 | —$CH_3$ | H | —$CH_2O$—N=C(—$CH_3$)— | 1-methyl-2-imidazolyl | H | — |
| 300 | —$CH_3$ | —$CH_2OCH_3$ | —$CH_2O$—N=C(—$CH_3$)— | 1-methyl-2-imidazolyl | H | — |
| 301 | —$CH_3$ | H | —$CH_2O$—N=C(—$CH_3$)— | 2-benzofuryl | H | — |
| 302 | —$CH_3$ | —$CH_2OCH_3$ | —$CH_2O$—N=C(—$CH_3$)— | 2-benzofuryl | H | — |
| 303 | —$CH_3$ | H | —$CH_2S$— | 3-chloro-5-trifluoromethyl-2-pyridyl | 4-(2-chloro-4-trifluoromethyl)-phenoxy | — |
| 304 | —$CH_3$ | —$CH_2OCH_3$ | —$CH_2S$— | 3-chloro-5-trifluoromethyl-2-pyridyl | 4-(2-chloro-4-trifluoromethyl)-phenoxy | — |
| 305 | —$CH_3$ | H | —$CH_2O$—N=C(—$OCH_3$)— | phenyl | H | m.p. 69–72° C. |
| 306 | —$CH_3$ | —$CH_2OCH_3$ | —$CH_2O$—N=C(—$OCH_3$)— | phenyl | H | viscous liquid |
| 307 | —$CH_3$ | H | —$CH_2O$—N=C(—N($CH_3$)$_2$)— | phenyl | H | — |
| 308 | —$CH_3$ | —$CH_2OCH_3$ | —$CH_2O$—N=C(—N($CH_3$)$_2$)— | phenyl | H | — |
| 309 | —$CH_3$ | H | —$CH_2O$—N=C(-piperidinyl)— | phenyl | H | — |
| 310 | —$CH_3$ | —$CH_2OCH_3$ | —$CH_2O$—N=C(-piperidinyl)— | phenyl | H | — |

TABLE 2-continued

Structure (I):
Benzene ring with positions labeled 1-6. Position 1 has N(R²)CO₂R¹, position 2 has Z-R³, position 4 has A.

| Compound No. | R¹ | R² | Z | R³ | A | Physical Properties |
|---|---|---|---|---|---|---|
| 311 | —CH₃ | H | —CH₂O—N=C(-pyrrolidin-1-yl)— | phenyl | H | — |
| 312 | —CH₃ | —CH₂OCH₃ | —CH₂O—N=C(-pyrrolidin-1-yl)— | phenyl | H | — |
| 313 | —CH₃ | H | —CH₂O—N=C(-1,2,4-triazol-1-yl)— | phenyl | H | — |
| 314 | —CH₃ | —CH₂OCH₃ | —CH₂O—N=C(-1,2,4-triazol-1-yl)— | phenyl | H | — |
| 315 | —CH₃ | H | —CH₂O—N=C(-imidazol-1-yl)— | phenyl | H | — |
| 316 | —CH₃ | —CH₂OCH₃ | —CH₂O—N=C(-imidazol-1-yl)— | phenyl | H | — |
| 317 | —CH₃ | H | —CH₂O—N=C(CH₃)— | 2-benzothienyl | H | — |
| 318 | —CH₃ | —CH₂OCH₃ | —CH₂O—N=C(CH₃)— | 2-benzothienyl | H | — |
| 319 | —CH₃ | —CH₂OCH₂CH₃ | —CH₂O—N=C(CH₃)— | phenyl | H | m.p. 59–61° C. |
| 320 | —CH₃ | —CH₃ | —CH₂O—N=C(CH₃)— | phenyl | H | m.p. 47–48° C. |
| 321 | —CH₃ | —CH₂CH₃ | —CH₂O—N=C(CH₃)— | phenyl | H | viscous liquid |
| 322 | —CH₃ | —CH₂CH₂CH₃ | —CH₂O—N=C(CH₃)— | phenyl | H | m.p. 68–70° C. |

TABLE 2-continued (I)

| Compound No. | R¹ | R² | Z | R³ | A | Physical Properties |
|---|---|---|---|---|---|---|
| 323 | —CH₃ | —CH₂CH₃ | —CH₂O—N=C(CH₃)— | 3,4-methylenedioxyphenyl | H | viscous liquid |
| 324 | —CH₃ | —CH₃ | —CH₂O—N=C(CH₃)— | 3,4-methylenedioxyphenyl | H | m.p. 90–92° C. |
| 325 | —CH₃ | H | —CH₂O—N=C(CH₃)— | 3-isopropoxyphenyl | H | m.p. 88–90° C. |
| 326 | —CH₃ | —CH₂OCH₃ | —CH₂O—N=C(CH₃)— | 3-isopropoxyphenyl | H | viscous liquid |
| 327 | —CH₃ | H | —CH₂O—N=C(CH₃)— | 5-trifluoromethyl-2-pyridyl | H | m.p. 126–128° C. |
| 328 | —CH₃ | —CH₂OCH₃ | —CH₂O—N=C(CH₃)— | 5-trifluoromethyl-2-pyridyl | H | m.p. 77–79° C. |
| 329 | —CH₃ | H | —CH₂O—N=C(CH₃)— | 1,2,3,4-tetrahydro-6-naphthyl | H | m.p. 109–111° C. |
| 330 | —CH₃ | —CH₂OCH₃ | —CH₂O—N=C(CH₃)— | 1,2,3,4-tetrahydro-6-naphthyl | H | m.p. 72–74° C. |
| 331 | —CH₃ | H | —CH₂O—N=C(CH₃)— | 5-indanyl | H | m.p. 119–121° C. |
| 332 | —CH₃ | —CH₂OCH₃ | —CH₂O—N=C(CH₃)— | 5-indanyl | H | m.p. 40–47° C. |
| 333 | —CH₃ | —CH₂OCH₂CH₂OCH₃ | —CH₂O—N=C(CH₃)— | phenyl | H | viscous liquid |
| 334 | —CH₃ | H | —CH₂O—N=C(CH₃)— | 2,3-dihydro-5-benzofuryl | H | m.p. 111–114° C. |
| 335 | —CH₃ | —CH₂OCH₃ | —CH₂O—N=C(CH₃)— | 2,3-dihydro-5-benzofuryl | H | viscous liquid |
| 336 | —CH₃ | H | —CH₂O—N=C(CH₃)— | 4-methoxy-3-methyl phenyl | H | m.p. 110–112° C. |
| 337 | —CH₃ | —CH₂OCH₃ | —CH₂O—N=C(CH₃)— | 4-methoxy-3-methyl phenyl | H | viscous liquid |
| 338 | —CH₃ | H | —CH₂O—N=C(CH₃)— | 3-(1-pyrrolyl)phenyl | H | m.p. 109–110° C. |

TABLE 2-continued

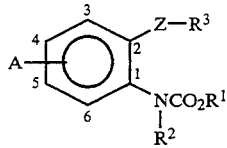
(I)

| Compound No. | R¹ | R² | Z | R³ | A | Physical Properties |
|---|---|---|---|---|---|---|
| 339 | —CH₃ | —CH₂OCH₃ | —CH₂O—N=C(CH₃)— | 3-(1-pyrrolyl)phenyl | H | viscous liquid |
| 340 | —CH₃ | H | —CH₂O—N=C(CH₃)— | 4-ethoxyphenyl | H | m.p. 134–135° C. |
| 341 | —CH₃ | —CH₂OCH₃ | —CH₂O—N=C(CH₃)— | 4-ethoxyphenyl | H | viscous liquid |
| 342 | —CH₃ | H | —CH₂O—N=C(CH₃)— | 4-ethoxy-3-methoxy-phenyl | H | m.p. 140–141° C. |
| 343 | —CH₃ | —CH₂OCH₃ | —CH₂O—N=C(CH₃)— | 4-ethoxy-3-methoxy-phenyl | H | viscous liquid |
| 344 | —CH₃ | H | —CH₂O—N=C(CH₃)— | 4-isopropoxyphenyl | H | m.p. 83–85° C. |
| 345 | —CH₃ | —CH₂OCH₃ | —CH₂O—N=C(CH₃)— | 4-isopropoxyphenyl | H | viscous liquid |
| 346 | —CH₃ | H | —CH₂O—N=C(CH₃)— | 3,4-(difluoromethyl-enedioxy)phenyl | H | — |
| 347 | —CH₃ | —CH₂OCH₃ | —CH₂O—N=C(CH₃)— | 3,4-(difluoromethyl-enedioxy)phenyl | H | — |
| 348 | —CH₃ | H | —CH₂O— | 3-(3-chloro-5-tri-fluoromethyl-2-pyridyloxy)phenyl | H | m.p. 121–123° C. |
| 349 | —CH₃ | —CH₂OCH₃ | —CH₂O— | 3-(3-chloro-5-tri-fluoromethyl-2-pyridyloxy)phenyl | H | viscous liquid |
| 350 | —CH₃ | H | —CH₂O—N=C(CH₃)— | 2,3-dihydro-5-benzo-thienyl | H | — |
| 351 | —CH₃ | —CH₂OCH₃ | —CH₂O—N=C(CH₃)— | 2,3-dihydro-5-benzo-thienyl | H | — |
| 352 | —CH₃ | H | —CH₂O—N=C(CH₃)— | 3-chloro-4-methoxy-phenyl | H | m.p. 170–173° C. |
| 353 | —CH₃ | —CH₂OCH₃ | —CH₂O—N=C(CH₃)— | 3-chloro-4-methoxy-phenyl | H | viscous liquid |
| 354 | —CH₃ | H | —CH₂O—N=C(CH₃)— | 3,4-(dichloromethyl-enedioxy)phenyl | H | — |
| 355 | —CH₃ | —CH₂OCH₃ | —CH₂O—N=C(CH₃)— | 3,4-(dichloromethyl-enedioxy)phenyl | H | — |

TABLE 2-continued $$\text{(I)}$$

Structure: benzene ring with positions 1-6; position 1 bears $NCO_2R^1$ with $R^2$; position 2 bears $Z-R^3$; position 5 bears $A$.

| Compound No. | $R^1$ | $R^2$ | Z | $R^3$ | A | Physical Properties |
|---|---|---|---|---|---|---|
| 356 | —$CH_3$ | H | —$CH_2O$—N=C(—$CH_3$)— | 3,4-(dimethylmethylenedioxy)phenyl | H | m.p. 119–121° C. |
| 357 | —$CH_3$ | —$CH_2OCH_3$ | —$CH_2O$—N=C(—$CH_3$)— | 3,4-(dimethylmethylenedioxy)phenyl | H | viscous liquid |
| 358 | —$CH_3$ | H | —$CH_2O$—N=C(—$CH_3$)— | 3,4-(methoxymethylenedioxy)phenyl | H | — |
| 359 | —$CH_3$ | —$CH_2OCH_3$ | —$CH_2O$—N=C(—$CH_3$)— | 3,4-(methoxymethylenedioxy)phenyl | H | — |
| 360 | —$CH_3$ | H | —$CH_2O$—N=C(—$CH_3$)— | 3-methyl-2-oxo-2,3-dihydro[1,3]benzoxazol-5-yl | H | — |
| 361 | —$CH_3$ | —$CH_2OCH_3$ | —$CH_2O$—N=C(—$CH_3$)— | 3-methyl-2-oxo-2,3-dihydro[1,3]benzoxazol-5-yl | H | — |
| 362 | —$CH_3$ | H | —$CH_2O$—N=C(—$CH_3$)— | 4-methyl-3-oxo-2,3-dihydro[1,4]benzoxazin-6-yl | H | — |
| 363 | —$CH_3$ | —$CH_2OCH_3$ | —$CH_2O$—N=C(—$CH_3$)— | 4-methyl-3-oxo-2,3-dihydro[1,4]benzoxazin-6-yl | H | — |
| 364 | —$CH_3$ | H | —$CH_2O$—N=C(—$CH_3$)— | 4-methyl-3-oxo-2,3-dihydro[1,4]benzothiazin-6-yl | H | — |
| 365 | —$CH_3$ | —$CH_2OCH_3$ | —$CH_2O$—N=C(—$CH_3$)— | 4-methyl-3-oxo-2,3-dihydro[1,4]benzothiazin-6-yl | H | — |
| 366 | —$CH_3$ | —$CH_2SCH_3$ | —$CH_2O$—N=C(—$CH_3$)— | phenyl | H | viscous liquid |
| 367 | —$CH_3$ | H | —$CH_2O$—N=C(—$CH_3$)— | benzoyl | H | viscous liquid |
| 368 | —$CH_3$ | —$CH_2OCH_3$ | —$CH_2O$—N=C(—$CH_3$)— | benzoyl | H | viscous liquid |
| 369 | —$CH_3$ | H | —$CH_2O$—N=C(—$CH_3$)— | 4-(methylsulfinyl)phenyl | H | m.p. 120–122° C. |
| 370 | —$CH_3$ | —$CH_2OCH_3$ | —$CH_2O$—N=C(—$CH_3$)— | 4-(methylsulfinyl)phenyl | H | viscous liquid |
| 371 | $CH_3$ | H | —$CH_2O$—N=C(—$CH_3$)— | 4-(methylsulfonyl)phenyl | H | m.p. 138–141° C. |

TABLE 2-continued $$\underset{R^2}{\overset{}{\underset{|}{N}}}\text{CO}_2R^1 \quad \text{structure (I) with positions 1-6, Z-R}^3 \text{ at position 2, A at position 5}$$

| Compound No. | $R^1$ | $R^2$ | Z | $R^3$ | A | Physical Properties |
|---|---|---|---|---|---|---|
| 372 | CH$_3$ | —CH$_2$OCH$_3$ | —CH$_2$O—N=C(CH$_3$)— | 4-(methylsulfonyl)phenyl | H | viscous liquid |
| 373 | —CH$_3$ | H | —CH$_2$O—N=C(CH$_3$)— | 3,4,5-trimethoxyphenyl | H | viscous liquid |
| 374 | —CH$_3$ | —CH$_2$OCH$_3$ | —CH$_2$O—N=C(CH$_3$)— | 3,4,5-trimethoxyphenyl | H | viscous liquid |
| 375 | —CH$_3$ | —CH$_2$OCH$_3$ | —CH$_2$O—N=C(CH$_3$)— | 5-indanyl | H | viscous liquid |
| 376 | —CH$_3$ | —CH$_2$OCH$_3$ | —CH$_2$O— | 2,4-dichlorophenyl | H | viscous liquid |
| 377 | —CH$_3$ | H | —CH$_2$O— | 2,4-dimethylphenyl | H | — |
| 378 | —CH$_3$ | —CH$_2$OCH$_3$ | —CH$_2$O— | 2,4-dimethylphenyl | H | — |
| 379 | —CH$_3$ | H | —CH$_2$O—N=C(CH$_3$)— | 3,4-dimethylphenyl | H | m.p. 112–114° C. |
| 380 | —CH$_3$ | —CH$_2$OCH$_3$ | —CH$_2$O—N=C(CH$_3$)— | 3,4-dimethylphenyl | H | viscous liquid |

In Table 2, the hyphen on the right side of Z represents a bond Directed toward $R^3$.

$^1$H-NMR data for Compound No. 4 (in CDCl$_3$): 3.27 (s, 3H), 3.67 (s, 3H), 4.47 (s, 2H), 7.13–7.62 (m, 4H), 7.73 (d, 1H), 8.60 (d, 1H)

$^1$H-NMR data for Compound No. 11 (in CDCl$_3$): 2.25 (t, 1H), 3.67 (s, 3H), 4.28 (d, 2H), 4.45 (s, 2H), 7.13–7.60 (m, 4H), 7.68 (d, 1H), 8.58 (d, 1H)

$^1$H-NMR data for Compound No. 20 (in CDCl$_3$): 3.40 (s, 3H), 3.63 (s, 3H), 4.50 (s, 2H), 4.58 (dd, 2H), 7.17–7.57 (m, 4H), 7.93 (d, 1H), 8.73 (d, 1H)

$^1$H-NMR data for Compound No. 21 (in CDCl$_3$): 2.23 (t, 1H), 3.70 (s, 3H), 4.38 (ddd, 2H), 4.53 (s, 2H), 7.18–7.63 (m, 4H), 8.00 (d, 1H), 8.80 (d, 1H)

$^1$H-NMR data for Compound No. 27 (in CDCl$_3$): 3.42 (s, 3H), 3.65 (s, 3H), 4.33 (s, 2H), 4.90 (dd, 2H), 7.10–7.50 (m, 4H), 7.43 (d, 1H), 8.20 (d, 1H)

$^1$H-NMR data for Compound No. 40 (in CDCl$_3$): 3.43 (s, 3H), 3.68 (s, 3H), 4.58 (s, 2H), 4.95 (dd, 2H), 7.07–7.88 (m, 8H)

$^1$H-NMR data (in CDCl$_3$) of Compound No. 44: 3.37 (s, 3H), 3.58 (s, 3H), 4.12 (s, 2H), 4.80 (dd, 2H), 6.97–7.37 (m, 8H)

$^1$H-NMR data for Compound No. 53 (in CDCl$_3$): 3.40 (s, 3H), 3.62 (s, 3H), 4.93 (dd, 2H), 6.85–7.77 (m, 10H)

$^1$H-NMR data for Compound No. 63 (in CDCl$_3$): 3.42 (s, 3H), 3.53 (s, 3H), 3.67 (s, 3H), 4.57 (s, 2H), 4.98 (dd, 2H), 7.07–7.62 (m, 7H)

$^1$H-NMR data for Compound No. 67 (in CDCl$_3$): 3.75 (s, 3H), 4.47 (s, 2H), 4.52 (dd, 2H), 7.23–7.67 (m, 4H), 7.75 (d, 1H), 8.60 (d, 1H)

$^1$H-NMR data for Compound No. 92 (in CDCl$_3$): 2.18 (s, 3H), 3.63 (s, 3H), 4.47 (s, 2H), 4.80 (dd, 2H), 7.17–7.67 (m, 4H), 7.75 (dd, 1H), 8.60 (dd, 1H)

$^1$H-NMR data for Compound No. 132 (in CDCl$_3$): 2.20 (s, 3H), 3.40 (s, 3H), 3.63 (s, 3H), 4.93 (dd, 2H), 5.16 (s, 2H), 7.20–7.67 (m, 9H)

$^1$H-NMR data for Compound No. 159 (in CDCl$_3$): 2.33 (s, 3H), 3.13 (s, 3H), 3.70 (s, 3H), 4.98 (dd, 2H), 5.20 (s, 2H), 7.26–7.90 (m, 6H), 8.50 (d, 2H)

$^1$H-NMR data for Compound No. 193 (in CDCl$_3$): 2.23 (s, 3H), 2.33 (s, 3H), 3.43 (s, 3H), 3.70 (s, 3H), 5.00 (dd, 2H), 5.17 (s, 2H), 7.10–7.50 (m, 8H)

$^1$H-NMR data for Compound No. 202 (in CDCl$_3$): 2.27 (s, 3H), 3.43 (s, 3H), 3.67 (s, 3H), 5.00 (dd, 2H), 5.27 (s, 2H), 7.16–8.07 (m, 6H), 8.90 (d, 1H)

$^1$H-NMR data for Compound No. 217 (in CDCl$_3$): 2.23 (s, 3H), 3.43 (s, 3H), 3.70 (s, 3H), 3.80 (s, 3H), 5.03 (dd, 2H), 5.20 (s, 2H), 6.77–7.63 (m, 8H)

$^1$H-NMR data for Compound No. 224 (in CDCl$_3$): 2.20 (s, 3H), 3.47 (s, 3H), 3.73 (s, 3H), 5.00 (dd, 2H), 5.17 (s, 2H), 5.97 (s, 2H), 6.73–7.60 (m, 7H)

1H-NMR data for Compound No. 227 (in CDCl$_3$): 2.17 (s, 3H), 3.40 (s, 3H), 3.63 (s, 3H), 4.17 (s, 4H), 4.93 (dd, 2H), 5.10 (s, 2H), 6.67–7.53 (m, 7H)

$^1$H-NMR data for Compound No. 240 (in CDCl$_3$): 2.33 (s, 3H), 3.43 (s, 3H), 3.67 (s, 3H), 5.00 (dd, 2H), 5.20 (s, 2H), 7.23–7.90 (m, 7H), 8.50 (d, 1H)

$^1$H-NMR data for Compound No. 321 (in CDCl$_3$): 1.13 (t, 3H), 2.20 (s, 3H), 3.05–3.88 (5H), 5.10 (s, 2H), 7.00–7.73 (m, 9H)

¹H-NMR data for Compound No. 323 (in CDCl₃):
1.18 (t, 3H), 2.23 (s, 3H), 3.50–3.90 (5H), 5.13 (s, 2H), 5.93 (s, 2H), 6.68–7.62 (m, 7H)

¹H-NMR data for Compound No. 328 (in CDCl₃):
2.36 (s, 3H), 3.47 (s, 3H), 3.73 (s, 3H), 5.05 (dd, 2H), 5.30 (s, 2H), 7.27–8.13 (m, 6H), 8.80–8.87 (m, 1H)

¹H-NMR data for Compound No. 332 (in CDCl₃):
1.90–2.23 (5H), 2.80–3.03 (t, 4H), 3.46 (s, 3H), 3.70 (s, 3H), 5.00 (dd, 2H), 5.18 (s, 2H), 7.10–7.60 (m, 7H)

¹H-NMR data for Compound No. 335 (in CDCl₃):
2.20 (s, 3H), 3.17 (t, 2H), 3.43 (s, 3H), 3.67 (s, 3H), 4.53 (t, 3H), 5.00 (dd, 2H), 5.10 (s, 2H), 6.65 (d, 1H), 7.20–7.50 (m, 6H)

¹H-NMR data for Compound No. 337 (in CDCl₃):
2.20 (s, 6H), 3.43 (s, 3H), 3.67 (s, 3H), 3.80 (s, 3H), 5.00 (dd, 2H), 5.13 (s, 2H), 6.73 (d, 2H), 7.23–7.53 (m, 6H)

¹H-NMR data for Compound No. 343 (in CDCl₃):
1.44 (t, 3H), 2.24 (s, 3H), 3.42 (s, 3H), 3.66 (s, 3H), 3.86 (s, 3H), 4.10 (q, 2H), 5.00 (dd, 2H), 5.15 (s, 2H), 6.70–7.60 (m, 6H)

¹H-NMR data for Compound No. 345 (in CDCl₃):
1.30 (d, 6H), 2.19 (s, 3H), 3.42 (s, 3H), 3.65 (s, 3H), 4.20–5.00 (m, 3H), 5.12 (s, 2H), 6.73–7.60 (m, 8H)

A description will now be made of Test Examples of testing the compound of the present invention as an agricultural and horticultural fungicide. The evaluation of performance was made according to the following ratings unless otherwise specified.

[Criteria of Evaluation]

The control effect was visually observed in terms of the degree of disease outbreak on test plant on the day of observation to give one of the following five ratings as an index of control:

| Rating | Degree of Disease Outbreak |
| --- | --- |
| 5 | No lesions are recognizable at all. |
| 4 | The Area, number or length of lesions is less than 10% of that in the non-treated plot. |
| 3 | The Area, number or length of lesions is less than 40% of that in the non-treated plot. |
| 2 | The Area, number or length of lesions is less than 70% of that in the non-treated plot. |
| 1 | The Area, number or length of lesions is 70% or more of that in the non-treated plot. |

Test Example 1

[Test on Preventive Effect against Cucumber Powdery Mildew]

Cucumber (cultivar: Suyo) was cultivated in a polyethylene pot having a diameter of 7.5 cm. When the cucumber reached a one-leaf stage, it was sprayed with 10 ml of a solution having predetermined active ingredient concentration through a spray gun. The pot was kept in a constant-temperature chamber at 22° to 24° C. for about 24 hours, after which the cucumber was dusted and inoculated with conidia of fungi of powdery mildew (*Sphaerotheca fuliginea*). Seventh to thirteenth day after the inoculation, the area of lesions on the first leaf was examined to find a rating as the index of control according to the above-mentioned criteria for evaluation. The results were as follows.

| Rating | Compound No. (Active Ingredient: 500 ppm) |
| --- | --- |
| 5 | 1, 11, 19, 26, 32, 46, 52, 56, 57, 94, 95, 103, 107, 109, 110, 111, 114, 116, 119, 120, 121, |

-continued

| Rating | Compound No. (Active Ingredient: 500 ppm) |
| --- | --- |
| | 122, 123, 128, 129, 131, 133, 134, 137, 138, 139, 141, 142, 143, 147, 149, 150, 151, 152, 153, 154, 156, 158, 160, 163, 165, 172, 177, 187, 188, 189, 190, 191, 192, 194, 198, 200, 201, 203, 204, 206, 208, 212, 215, 216, 217, 219, 225, 228, 230, 235, 237, 239, 240, 243, 244, 245, 247, 248, 250, 251, 252, 261, 282, 320, 322, 327, 328, 330, 344, 345 |
| 4 | 2, 5, 41, 45, 99, 105, 108, 130, 132, 140, 148, 157, 159, 168, 169, 193, 197, 199, 202, 205, 207, 226, 229, 236, 249, 264, 281, 289, 290, 323, 325, 326, 329, 341 |

Compounds Nos. 214 and 218 both exhibited a rating of 5 as the index of control and Compound No. 343 exhibited a rating of 4 as the index of control when the active ingredient concentrations of the solutions were 250 ppm.

Test Example 2

[Test on Preventive Effect against Cucumber Anthracnose]

Cucumber (cultivar: Suyo) was cultivated in a polyethylene pot having a diameter of 7.5 cm. When the cucumber reached a two-leaf stage, it was sprayed with 10 ml of a solution having predetermined active ingredient concentration through a spray gun. The pot was kept in a constant-temperature chamber at 22° to 24° C. for about 24 hours, after which the cucumber was sprayed and inoculated with a spore suspension of fungi of anthracnose (*Collectotrichum lagenarium*). Fifth to ninth day after the inoculation, the area of lesions on the first leaf was examined to find a rating as the index of control according to the above-mentioned criteria for evaluation. The results were as follows.

| Rating | Compound No. (Active Ingredient: 500 ppm) |
| --- | --- |
| 5 | 4, 5, 7, 9, 27, 52, 53, 56, 109 |
| 4 | 3, 8, 11, 145, 289 |

Compound No. 57 exhibited a rating of 5 as the index of control when the active ingredient concentration of the solution was 250 ppm.

Test Example 3

[Test on Preventive Effect against Cucumber Downy Mildew]

Cucumber (cultivar: Suyo) was cultivated in a polyethylene pot having a diameter of 7.5 cm. When the cucumber reached a two-leaf stage, it was sprayed with 10 ml of a solution having predetermined active ingredient concentration through a spray gun. The pot was kept in a constant-temperature chamber at 22° to 24° C. for about 24 to 48 hours, after which the cucumber was sprayed and inoculated with a spore suspension of fungi of downy mildew (*Pseudoperonospora cubensis*). Fourth to eighth day after the inoculation, the area of lesions on the first leaf was examined to find a rating as the index of control according to the aforementioned criteria for evaluation. The results were as follows.

| Rating | Compound No. (Active Ingredient: 500 ppm) |
| --- | --- |
| 5 | 1, 3, 4, 5, 6, 7, 8, 9, 11, 19, 20, 21, 22, 23, 25, 26, 27, 33, 34, 35, 37, 39, 40, 41, 42, 43, |

-continued

| Rating | Compound No. (Active Ingredient: 500 ppm) |
|---|---|
|  | 46, 47, 49, 50, 51, 93, 95, 98, 101, 113, 124, 131, 134, 137, 161, 162, 170, 198, 201, 209, 220, 221, 226, 234, 247, 258, 327 |
| 4 | 2, 24, 32, 44, 45, 48, 54, 97, 99, 102, 104, 171, 193, 224 |

Compound No. 200 exhibited a rating of 4 as the index of control when the active ingredient concentration of the solution was 250 ppm.

Test Example 4

[Test on Preventive Effect against Rice Blast]

Rice plant (cultivar: Koshihikari) was cultivated in a polyethylene pot having a diameter of 7.5 cm. When the rice plant reached a four-leaf stage, it was sprayed with 20 ml of a solution having a predetermined active ingredient concentration through a spray gun. The pot was kept in a constant-temperature chamber at 22° to 24° C. for about 8 to 24 hours, after which the rice plant was sprayed and inoculated with a spore suspension of fungi of blast (*Pyricularia oryzae*). Fourth to eighth day after the inoculation, the number of lesions was examined to find a rating as the index of control according to the aforementioned criteria for evaluation. The results were as follows:

| Rating | Compound No. (Active Ingredient: 500 ppm) |
|---|---|
| 5 | 2, 3, 11, 14, 15, 20, 23, 48, 49, 57, 58, 92, 120, 139, 162, 166, 196, 205, 224, 225, 227, 230, 257, 261, 276, 282, 284, 290, 321, 322, 329, 338, 339, 352 |
| 4 | 1, 5, 6, 9, 21, 25, 28, 29, 36, 45, 46, 50, 51, 54, 67, 132, 135, 136, 138, 141, 142, 143, 153, 159, 164, 167, 170, 171, 172, 176, 177, 192, 211, 212, 217, 221, 228, 229, 235, 236, 238, 244, 248, 274, 332, 333, 335, 337 |

Compounds Nos. 40 and 7 exhibited ratings of 5 and 4, respectively, as the indices of control when the active ingredient concentrations of the solutions were 250 ppm.

Test Example 5

[Test on Curative Effect against Rice Blast]

Rice plant (cultivar: Koshihikari) was cultivated in a polyethylene pot having a diameter of 7.5 cm. When the rice plant reached a four-leaf stage, it was sprayed and inoculated with a spore suspension of fungi of blast (*Pyricularia oryzae*). The pot was kept in a constant-temperature chamber at 22° to 24° C. for about 24 hours, after which the rice plant was sprayed with 20 ml of a solution having a Compound No. 3 (active ingredient) concentration of 500 ppm through a spray gun. Fifth day after the inoculation, the number of lesions was examined to find a rating of 4 as the index of control according to the aforementioned criteria for evaluation.

Test Example 6

[Test on Preventive Effect against Oat Crown Rust]

Oat (cultivar: Zenshin) was cultivated in a polyethylene pot having a diameter of 7.5 cm. When the oat reached a two-leaf stage, it was sprayed with 20 ml of a solution having a predetermined active ingredient concentration through a spray gun. The pot was kept in a constant-temperature chamber at 22° to 24° C. for about 8 to 24 hours, after which the rice plant was dusted and inoculated with conidia of fungi of crown rust (*Puccinia coronata*). Ninth to fifteenth day after the inoculation, the area of lesions on the second leaf was examined to find a rating as the index of control according to the aforementioned criteria for evaluation. The results were as follows:

| Rating | Compound No. (Active Ingredient: 500 ppm) |
|---|---|
| 5 | 2, 3, 4, 5, 7, 11, 28, 44, 51, 53, 57, 67, 94, 101, 103, 105, 107, 108, 111, 114, 116, 118, 119, 120, 121, 122, 123, 132, 133, 136, 138, 150, 151, 153, 154, 159, 160, 166, 167, 187, 188, 190, 194, 196, 197, 204, 206, 215, 217, 219, 220, 223, 224, 251, 252, 276, 290, 321, 323, 326, 339 |
| 4 | 27, 29, 37, 40, 52, 56, 110, 115, 117, 124, 129, 135, 148, 157, 163, 165, 176, 199, 205, 208, 211, 216, 218, 238, 240, 244, 248, 250, 320, 328, 330, 341, 343, 345 |

Compounds Nos. 113 and 214 both exhibited a rating of 5 as the index of control when the active ingredient concentrations of the solutions were 250 ppm.

Test Example 7

[Test on Preventive Effect against Tomato Late Blight]

Tomato (cultivar: Ponderosa) was cultivated in a polyethylene pot having a diameter of 7.5 cm. When the tomato reached a four-leaf stage, it was sprayed with 10 ml of a solution having a predetermined active ingredient concentration through a spray gun. The pot was kept in a constant-temperature chamber at 22° to 24° C. for about 8 to 24 hours, after which the tomato plant was sprayed and inoculated with a zoosporangia suspension of fungi of late blight (*Phytophthora infestans*). Third to fifth day after the inoculation, the area of lesions was examined to find a rating as the index of control according to the aforementioned criteria for evaluation. The results were as follows:

| Rating | Compound No. (Active Ingredient: 500 ppm) |
|---|---|
| 5 | 1, 4, 11, 37, 39, 52, 53, 57, 63, 168, 191, 193, 246, 284 |
| 4 | 3, 5, 7, 8, 14, 40, 45, 61, 67, 152, 203, 352 |

Compound No. 51 exhibited a rating of 4 as the index of control when the active ingredient concentration of the solution was 125 ppm.

Test Example 8

[Test on Preventive Effect against Cucumber Gray Mold]

Cucumber (cultivar: Suyo) was cultivated in a polyethylene pot having a diameter of 7.5 cm. When the cucumber reached a two-leaf stage, it was sprayed with 10 ml of a solution having predetermined active ingredient concentration through a spray gun. The pot was kept in a constant-temperature chamber at 22° to 24° C. for about 24 hours, after which the first leaf was inoculated with a spore suspension of fungi of Benomyl and dicarboximide-sensitive gray mold (*Botrytis cinerea*) in a potato glucose decoction. Third day after the inoculation, the length of lesions was examined to find a rating as the index of control according to the above-mentioned criteria for evaluation. The results were as follows:

| Rating | Compound No. (Active Ingredient: 500 ppm) |
|---|---|
| 4 | 1, 57, 103, 132 |

Test Example 9

[Test on Preventive Effect against Rice Sheath Blight]

Rice plant (cultivar: Koshihikari) was cultivated in a polyethylene pot having a diameter of 7.5 cm. When the rice plant reached a five-leaf stage, it was sprayed with 20 ml of a solution having a Compound No. 349 (active ingredient) concentration of 500 ppm through a spray gun. The pot was kept in a constant-temperature chamber at 22° to 24° C. for about 24 hours, after which the rice plant was inoculated by putting in the sheath thereof a rice straw wherein fungi of sheath blight (Rhizoctonia solani) had been preliminarily incubated. The pot was kept in an inoculation chamber at a temperature of 28° C. and a humidity of 100% for 5 days. Thereafter, the length of lesions was examined to find a rating of 4 as the index of control according to the above-mentioned criteria for evaluation.

While the invention has been described in detail and with reference to specific embodiments thereof, it will be apparent to one skilled in the art that various changes and modifications can be made therein without departing from the spirit and scope thereof.

What is claimed is:

1. An N-phenylcarbamate compound represented by the following formula (I) or its salt

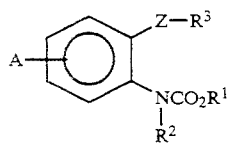

wherein $R^1$ is a $C_{1-6}$ alkyl group which may be substituted with at least one substituent selected from the group consisting of halogen, cyano, $C_{1-6}$ alkoxy, $C_{1-6}$ alkylthio, $C_{1-6}$ alkoxycarbonyl, $C_{1-6}$ alkylcarbonyl, $C_{3-6}$ cycloalkyl; $R^2$ is a substituent selected from the group consisting of a hydrogen atom, a $C_{1-6}$ alkyl group, a $C_{2-6}$ alkenyl group, a $C_{2-6}$ alkynyl group, a $C_{3-6}$ cycloalkyl group, and a $—COX^1$ group wherein each of the alkyl, the alkenyl, the alkynyl and the cycloalkyl groups may be substituted with at least one substituent selected from the group consisting of halogen, cyano, $C_{1-6}$ alkoxy, $C_{1-6}$ alkylthio, $C_{1-6}$ alkoxycarbonyl, $C_{1-6}$ alkylcarbonyl, $C_{3-6}$ cycloalkyl, $X^1$ is a substituent selected from the group consisting of a $C_{1-6}$ alkyl groups, a $C_{2-6}$ alkenyl group, a $C_{2-6}$ alkynyl group, a $C_{3-6}$ cycloalkyl group, and a $C_{1-6}$ alkoxy group wherein each of the alkyl, the alkenyl, the alkynyl, the cycloalkyl and the alkoxy groups may be substituted with at least one substituent selected from the group consisting of halogen, cyano, $C_{1-6}$ alkoxy, $C_{1-6}$ alkylthio, $C_{1-6}$ alkoxycarbonyl, $C_{1-6}$ alkylcarbonyl, $C_{3-6}$ cycloalkyl; Z is a $—CH_2O—N=C(R^4)—$ group, the right hyphen of which represents a bond directed toward $R^3$; $R^3$ is a substituent selected from the group consisting of a phenyl group, a pyridyl group, a benzothiazolyl group, a benzoxazolyl group, a benzimidazolyl group, an imidazopyridyl group, wherein each of the phenyl, pyridyl, benzothiazolyl, benzoxazolyl, benzimidazolyl and imidazopyridyl groups may be substituted with at least one substituent selected from the group consisting of halogen, a $C_{1-6}$ alkyl group which may be substituted with halogen, a nitro group, a cyano group, a $C_{1-6}$ alkoxycarbonyl group, a $C_{1-6}$ alkoxy group, a $C_{1-6}$ alkylthio group, an aryl group, and a carbamoyl group which may be substituted with at least one $C_{1-6}$ alkyl; $R^4$ is a hydrogen atom or a methyl group and A is a hydrogen atom.

2. An N-phenylcarbamate compound or its salt as claimed in claim 1, wherein $R^2$ is a substituent selected from the group consisting of a hydrogen atom, a $C_{1-6}$ alkyl group, a $C_{2-6}$ alkynyl group and a $—COX^1$ group wherein $X^1$ is a $C_{1-6}$ alkyl group.

3. An N-phenylcarbamate compound or its salt as claimed in claim 1, wherein $R^3$ is a substituent selected from the group consisting of a phenyl group and a pyridyl group.

4. An N-phenylcarbamate compound or its salt as claimed in claim 1, wherein $R^2$ is a $C_{1-6}$ alkyl group; Z is a $—CH_2O—N=C(R^4)—$ group; $R^3$ is a substituent selected from the group consisting of a phenyl group and a pyridyl group; and $R^4$ is a methyl group.

5. An N-phenylcarbamate compound or its salt where possible as claimed in claim 1, wherein $R^2$ is a methyl group, an ethyl group, or a methoxymethyl group; and $R^4$ is a methyl group.

6. An N-phenylcarbamate compound or its salt as claimed in claim 1, wherein said N-phenylcarbamate compound is:

methyl  N-(methoxymethyl)-N-[2-[(α-methylbenzylidene)aminooxymethyl]phenyl]carbamate, methyl  N-(ethyl)-N-[2-[(α-methylbenzylidene)aminooxymethyl]phenyl]carbamate,

[methyl  N-(methoxymethyl)-N-[2-[[α-methyl-3,4-(methylenedioxy)benzylidene]aminooxymethyl]-phenyl]-carbamate, methyl N-(ethyl)-N-[2-[[α-methyl-3,4-(methylenedioxy)benzylidene]aminooxymethyl]phenyl]carbamate, ]

methyl  N-(methoxymethyl)-N-[2-[[α-methyl-4-(isopropoxy)benzylidene]aminooxymethyl]phenyl]-carbamate, methyl  N-(methoxymethyl)-N-[2-[[α-methyl-4-(ethoxy)-3-(methoxy)benzylidene]aminooxymethyl]phenyl]-carbamate, methyl  N-(methoxymethyl)-N-[2-[[α-methyl-4-(methoxy)-3-(methylbenzylidene]aminooxymethyl]-phenyl]-carbamate,

[methyl N-(methoxymethyl)-N-[2-[[1-(2,3-dihydro-5-benzofuryl)ethylidene]aminooxymethyl]phenyl]-carbamate, methyl  N-(methoxymethyl)-N-[2-[[1-(5-indanyl)ethylidene]aminooxymethyl]phenyl]carbamate,]

methyl  N-(methoxymethyl)-N-[2-[[1-(5-trifluoromethyl-2-pyridyl)ethylidene]aminooxymethyl]-phenyl]carbamate; or methyl  N-(methoxymethyl)-N-[2-[[1-(5-chloro-2-pyridyl)ethylidene]aminooxymethyl]phenyl]carbamate.

7. A biocidal composition for control of harmful organisms, comprising as an active ingredient an N-phenylcarbamate compound represented by the following formula (I) or its salt:

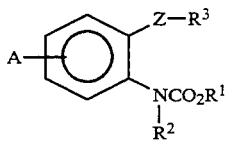 (I)

wherein $R^1$ is a $C_{1-6}$ alkyl group which may be substituted with at least one substituent selected from the group consisting of halogen, cyano, $C_{1-6}$ alkoxy, $C_{1-6}$ alkylthio, $C_{1-6}$ alkoxycarbonyl, $C_{1-6}$ alkylcarbonyl, and $C_{3-6}$ cycloalkyl; $R^2$ is a substituent selected from the group consisting of a hydrogen atom, a $C_{1-6}$ alkyl group, a $C_{2-6}$ alkenyl group, a $C_{2-6}$ alkynyl group, a $C_{3-6}$ cycloalkyl group, and a —$COX^1$ group wherein each of the alkyl, the alkenyl, the alkynyl and the cycloalkyl groups may be substituted with at least one substituent selected from the group consisting of halogen, cyano, $C_{1-6}$ alkoxy, $C_{1-6}$ alkylthio, $C_{1-6}$ alkoxycarbonyl, $C_{1-6}$ alkylcarbonyl, $C_{3-6}$ cycloalkyl, $X^1$ is a substituent selected from the group consisting of a $C_{1-6}$ alkyl group, a $C_{2-6}$ alkenyl group, a $C_{2-6}$ alkynyl group, a $C_{3-6}$ cycloalkyl group, and a $C_{1-6}$ alkoxy group wherein each of the alkyl, the alkenyl, the alkynyl, the cycloalkyl and the alkoxy groups may be substituted with at least one substituent selected from the group consisting of halogen, cyano, $C_{1-6}$ alkoxy, $C_{1-6}$ alkylthio, $C_{1-6}$ alkoxycarbonyl, $C_{1-6}$ alkylcarbonyl, $C_{3-6}$ cycloalkyl; $Z$ is a —$CH_2O$—$N$=$C(R^4)$— group, the right hyphen of each of which represents a bond directed toward $R^3$; $R^3$ is substituent selected from the group consisting of a phenyl group, a pyridyl group, a benzothiazolyl group, a benzoxazolyl group, a benzimidazolyl group, an imidazopyridyl group, wherein each of the phenyl, pyridyl, benzothiazolyl, benzoxazolyl, benzimidazolyl and imidazopyridyl groups may be substituted with at least one substituent selected from the group consisting of halogen, $C_{1-6}$ alkyl which may be substituted with halogen, nitro, cyano, $C_{1-6}$ alkoxycarbonyl, $C_{1-6}$ alkoxy, $C_{1-6}$ alkylthio, aryl, and carbamoyl which may be substituted with at least one $C_{1-6}$ alkyl; $R^4$ is a substituent selected from the group consisting of a hydrogen atom and a methyl group; and A is a hydrogen atom.

* * * * *